US012156734B2

(12) United States Patent
Shimizu et al.

(10) Patent No.: US 12,156,734 B2
(45) Date of Patent: Dec. 3, 2024

(54) SENSOR INSERTION DEVICE

(71) Applicant: PHC Holdings Corporation, Tokyo (JP)

(72) Inventors: Ryuji Shimizu, Ehime (JP); Fumiya Matsubara, Ehime (JP); Masahiro Kouge, Ehime (JP); Akira Nishio, Ehime (JP); Seiji Onishi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 262 days.

(21) Appl. No.: 17/425,867

(22) PCT Filed: Mar. 2, 2020

(86) PCT No.: PCT/JP2020/008737
§ 371 (c)(1),
(2) Date: Jul. 26, 2021

(87) PCT Pub. No.: WO2020/189243
PCT Pub. Date: Sep. 24, 2020

(65) Prior Publication Data
US 2022/0000398 A1 Jan. 6, 2022

(30) Foreign Application Priority Data

Mar. 20, 2019 (JP) ................................ 2019-052990
Mar. 20, 2019 (JP) ................................ 2019-052992
(Continued)

(51) Int. Cl.
*A61B 5/1473* (2006.01)
*A61B 5/1486* (2006.01)
(Continued)

(52) U.S. Cl.
CPC .......... *A61B 5/1473* (2013.01); *A61B 5/1486* (2013.01); *A61M 25/02* (2013.01); *A61M 37/00* (2013.01)

(58) Field of Classification Search
CPC ................ A61B 5/1473; A61B 5/1486; A61B 2560/0285; A61B 2562/247;
(Continued)

(56) References Cited

U.S. PATENT DOCUMENTS

2011/0288574 A1  11/2011 Curry et al.
2011/0319729 A1  12/2011 Donnay et al.
(Continued)

FOREIGN PATENT DOCUMENTS

CN   103690196   4/2014
CN   107106090   8/2017
(Continued)

OTHER PUBLICATIONS

International Search Report issued Apr. 28, 2020, in International (PCT) Application No. PCT/JP2020/008737, with English translation.
(Continued)

*Primary Examiner* — Yi-Shan Yang
*Assistant Examiner* — Kyle W. Kretzer
(74) *Attorney, Agent, or Firm* — Wenderoth, Lind & Ponack, L.L.P.

(57) ABSTRACT

A sensor insertion device comprises a lower case and an upper case. A base holder and a needle holder are disposed in the lower case. A needle holder raising mechanism is disposed above the needle holder. A sensor base having a sensor unit is held by the base holder. When the upper case is pushed down, the base holder and the needle holder move toward an opening on the lower surface side of the lower case, and the needle holder is raised by the needle holder
(Continued)

raising mechanism. A protrusion that holds the upper case on the lower case is provided to the upper case in a state in which the upper case has been pushed down until the opening on the lower surface side comes into contact with the skin.

8 Claims, 38 Drawing Sheets

(30) Foreign Application Priority Data

| Mar. 20, 2019 | (JP) | 2019-053080 |
| Mar. 20, 2019 | (JP) | 2019-053177 |
| Mar. 20, 2019 | (JP) | 2019-053181 |
| Mar. 27, 2019 | (JP) | 2019-061409 |

(51) Int. Cl.
*A61M 25/02* (2006.01)
*A61M 37/00* (2006.01)

(58) Field of Classification Search
CPC .............. A61B 5/6849; A61B 5/14503; A61B 2560/063; A61B 17/3468; A61B 5/14865; A61M 25/02; A61M 37/00
See application file for complete search history.

(56) References Cited

U.S. PATENT DOCUMENTS

| 2012/0010642 | A1 | 1/2012 | Lee et al. |
| 2012/0190941 | A1 | 7/2012 | Donnay et al. |
| 2012/0190942 | A1 | 7/2012 | Donnay et al. |
| 2012/0190943 | A1 | 7/2012 | Donnay et al. |
| 2012/0190951 | A1 | 7/2012 | Curry et al. |
| 2012/0179098 | A1 | 8/2012 | Donnay et al. |
| 2012/0197222 | A1 | 8/2012 | Donnay et al. |
| 2013/0150691 | A1 | 6/2013 | Pace et al. |
| 2014/0207102 | A1* | 7/2014 | Segal ................. A61M 5/3158 604/193 |
| 2015/0025338 | A1 | 1/2015 | Lee et al. |
| 2016/0030078 | A1 | 2/2016 | Lee et al. |
| 2016/0058474 | A1* | 3/2016 | Peterson ............ A61B 5/14503 600/347 |
| 2016/0128615 | A1 | 5/2016 | Curry et al. |
| 2017/0042457 | A1 | 2/2017 | Pace et al. |
| 2017/0112534 | A1* | 4/2017 | Schoonmaker .... A61B 5/14503 |
| 2017/0265791 | A1 | 9/2017 | Pace et al. |
| 2018/0008803 | A1* | 1/2018 | Muramatsu ....... A61M 25/0631 |
| 2018/0235520 | A1* | 8/2018 | Rao ...................... A61B 5/6849 |
| 2018/0317820 | A1 | 11/2018 | Pace et al. |
| 2019/0076073 | A1 | 3/2019 | Donnay et al. |
| 2019/0133638 | A1 | 5/2019 | Ii et al. |
| 2019/0298240 | A1 | 10/2019 | Lee et al. |
| 2020/0397358 | A1 | 12/2020 | Lee et al. |
| 2020/0405201 | A1 | 12/2020 | Ochi |
| 2020/0405208 | A1 | 12/2020 | Lee et al. |
| 2021/0000399 | A1 | 1/2021 | Curry et al. |
| 2021/0000400 | A1 | 1/2021 | Curry et al. |
| 2021/0007651 | A1 | 1/2021 | Donnay et al. |
| 2021/0022654 | A1 | 1/2021 | Curry et al. |
| 2021/0038137 | A1 | 2/2021 | Curry et al. |
| 2021/0068721 | A1 | 3/2021 | Pace et al. |
| 2021/0068722 | A1 | 3/2021 | Pace et al. |
| 2021/0113126 | A1 | 4/2021 | Donnay et al. |
| 2021/0161445 | A1 | 6/2021 | Donnay et al. |
| 2021/0169518 | A1 | 6/2021 | Shimizu et al. |
| 2022/0007973 | A1 | 1/2022 | Rso et al. |
| 2022/0151517 | A1 | 5/2022 | Rao et al. |
| 2023/0032816 | A1 | 2/2023 | Schoonmaker et al. |

FOREIGN PATENT DOCUMENTS

| CN | 108024716 | 5/2018 |
| JP | 2013-523216 | 6/2013 |
| JP | 2015-509011 | 3/2015 |
| JP | 2016-128031 | 7/2016 |
| WO | 2016/036924 | 3/2016 |
| WO | 2017/070360 | 4/2017 |
| WO | 2017/187943 | 11/2017 |
| WO | 2018/136898 | 7/2018 |
| WO | 2019/176324 | 9/2019 |
| WO | 2019/181199 | 9/2019 |

OTHER PUBLICATIONS

Extended European Search Report issued Jun. 27, 2022 in corresponding European Patent Application No. 20772637.3.
Office Action issued Nov. 15, 2023 in corresponding Chinese Patent Application No. 202080010946.X, with English-language translation (14 pages).

* cited by examiner

A–A' cross sectional-view

SENSOR INSERTION DEVICE

TECHNICAL FIELD

The present invention relates, for example, to a sensor insertion device for inserting a sensor unit for performing continuous blood glucose measurement into a human body.

BACKGROUND ART

Conventionally, when using this type of sensor insertion device, first, a sensor unit that is kept in a sterile state is attached to the sensor base of the sensor insertion device. After this, the sensor insertion device is pushed down toward the user's body. As a result, the sensor base is attached to the body and the sensor unit is inserted into the body (see, for example, Patent Literature 1).

CITATION LIST

Patent Literature

Patent Literature 1: Japanese Unexamined Patent Application Publication (Translation of PCT Application) No. 2015-509011

SUMMARY

Technical Problem

In the above-mentioned conventional example, the sensor base is held by the lower case, and the sensor insertion device is pushed down by pushing down the upper case covering the lower case from above.

However, even if the upper case is pushed down, the lower part of the lower case is exposed below the upper case, just as it was before being pushed down, leaving the user unsure whether the sensor insertion device has already been used, and therefore the user may try to mount the sensor base again using this used sensor insertion device. However, with a used sensor insertion device, a new sensor unit cannot be attached to the sensor base, and if the sensor unit is allowed to stand for a long time during that period, the sterilization measures taken for the sensor unit will have been wasted, and the measurement reliability will end up decreasing. Thus, in the conventional example, it was difficult to determine whether or not the sensor insertion device had been used, which made it extremely inconvenient to use.

It is therefore an object of the present invention to improve usage convenience of the sensor insertion device.

Solution to Problem

The sensor insertion device according to an embodiment of the present invention includes a lower case, an upper case, a base holder, a needle holder and a needle holder raising mechanism. The lower case formed in a cylindrical shape has an upper opening at the upper end and a lower opening at the lower end. The upper case formed in a cylindrical shape has an opening at the lower end and is closed on the upper surface, which covers the outer periphery of the lower case from above so as to be movable downward. The base holder is disposed inside the lower case and holds a sensor base having a sensor unit. The needle holder is disposed above the base holder inside the lower case. The needle holder raising mechanism is disposed above the needle holder inside the lower case and/or the upper case. When the upper case is pushed down, the base holder and the needle holder move toward the lower opening of the lower case. After this, the needle holder is raised by the needle holder raising mechanism. A holding mechanism is provided to the inner peripheral surface of the upper case and/or the outer peripheral surface of the lower case. The holding mechanism is configured to hold the upper case on the lower case in a state in which the upper case has been pushed down until the opening of the upper case hits the skin.

The sensor insertion device according to another embodiment of the present invention includes a lower case, an upper case, an upper position holding portion, a base holder and a holding mechanism. The lower case formed in a cylindrical shape has openings at the upper and lower ends respectively. The upper case formed in a cylindrical shape has an opening at the lower end, which covers the outer periphery of the lower case from above. The upper position holding portion holds the upper case at a specific upper position with respect to the lower case and exposes the lower case from the upper case. The base holder pre-holds a sensor base having a sensor unit and is disposed inside the lower case, and releases the sensor base when the upper case is pushed down from the upper position with respect to the lower case. The holding mechanism holds the upper case on the lower case in a state in which the upper case has been pushed down until the opening of the upper case is at substantially the same position as the lower opening of the lower case.

Advantageous Effects

In the present invention, since the sensor base having the sensor unit is held by the base holder, the user does not have to attach the sensor unit to the sensor base. When the upper case is pushed down, the sensor base is attached to the skin and the sensor unit is inserted into the user's body. When the upper case is pushed down until its opening comes into contact with the skin, the opening of the upper case is at substantially the same position as the lower opening of the lower case, and this state is maintained by the holding mechanism. It is readily apparent that the device has been used. Therefore, no attempt is made to use it again, and this greatly enhances work efficiency.

DESCRIPTION OF EMBODIMENTS

Figure 1:
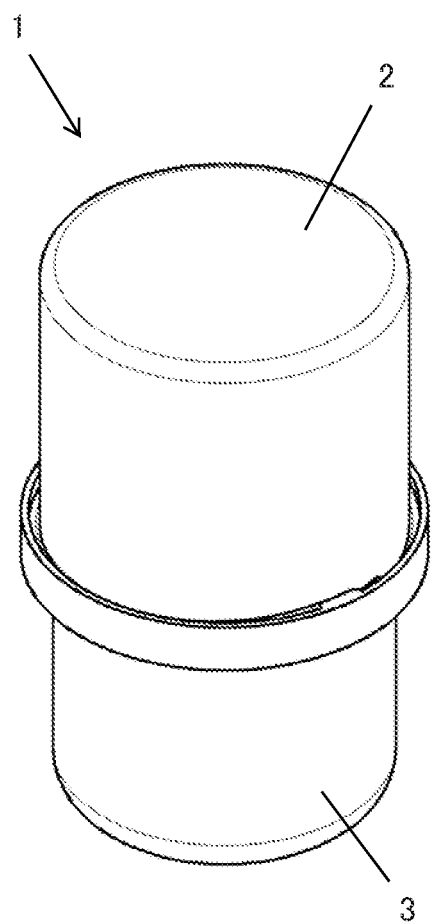
FIG. 1 is an oblique view of the state before use of the sensor insertion device according to an embodiment.

Embodiments will now be described with reference to the appended drawings. In the drawings, the same or corresponding elements are numbered the same, and redundant description is omitted. The sensor insertion device according to an embodiment is formed in a substantially cylindrical shape as an example. The "inner and outer directions" correspond to the radial direction of the sensor insertion device, the "inner peripheral side" is the side closer to the center in the radial direction, and the "outer peripheral side" is the side away from the center in the radial direction. The "up and down direction" corresponds to the axial direction of the sensor insertion device, and "below" refers to the direction toward the user's body when the sensor insertion device is used.

Figure 2:
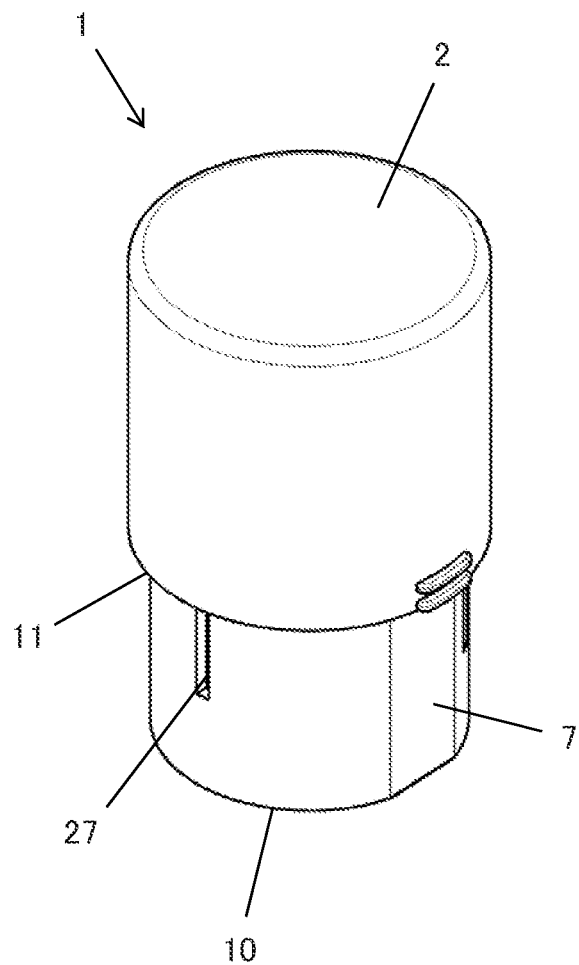
FIG. 2 is an oblique view of the sensor insertion device shown in FIG. 1 in a state in which a cap has been removed from the sensor insertion device.

FIGS. 1 and 2 are oblique views of the sensor insertion device 1 according to an embodiment. As shown in FIG. 2, the sensor insertion device 1 comprises an upper case 2 and a lower case 7. As shown in FIG. 1, prior to use, a cap 3 is detachably joined to the upper case 2 from below, and the lower case 7 is covered by the cap 3. A gasket (not shown) is provided at the joint between the upper case 2 and the cap 3. This seals the interior of the upper case 2 and the cap 3, and allows this interior to be kept in a sterile state.

Figure 3:
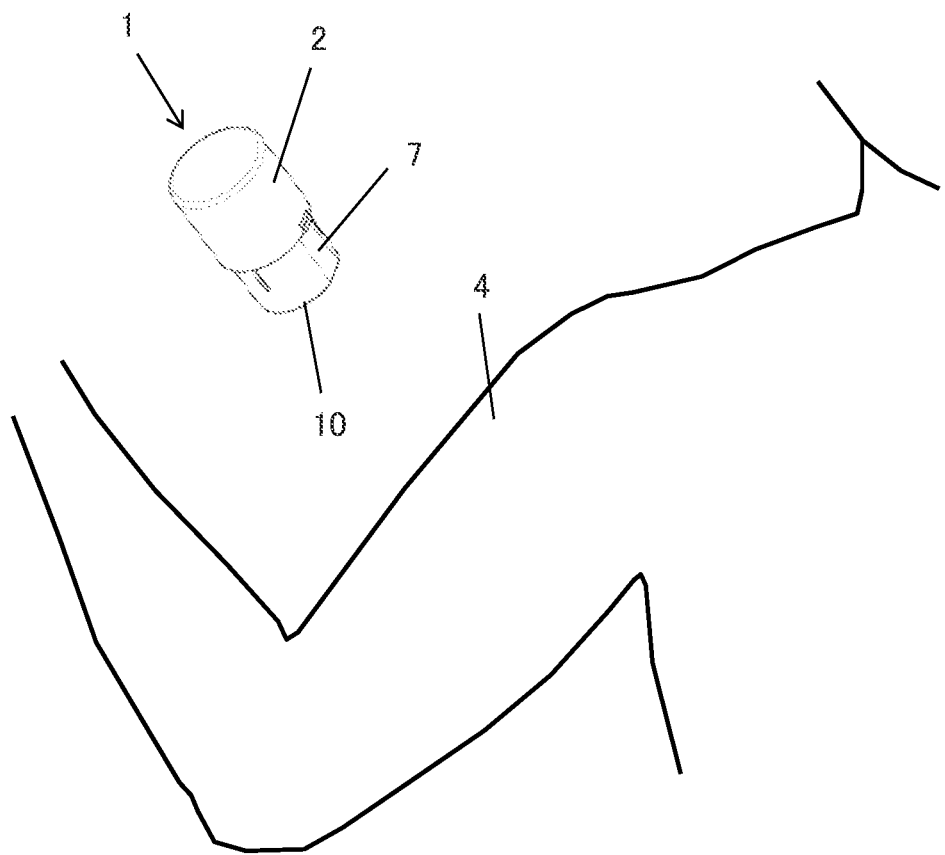
FIG. 3 is an oblique view of the usage state of the sensor insertion device in FIG. 2.
Figure 4:
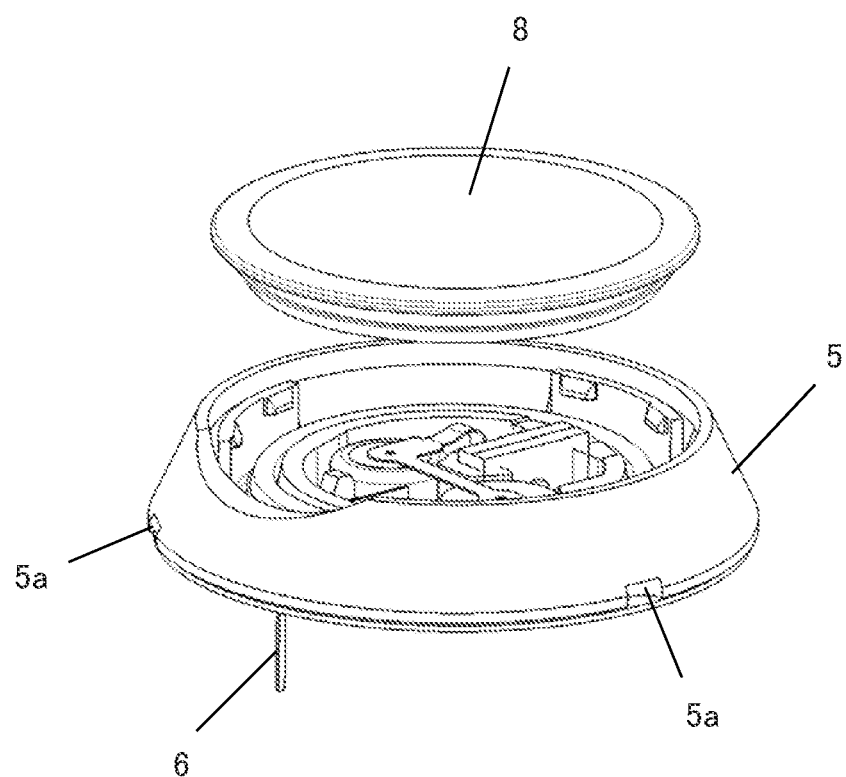
FIG. 4 is an oblique view of a biological information measurement device used in the sensor insertion device in FIG. 2.

As shown in FIGS. 2 and 3, in using the sensor insertion device 1, the user removes the cap 3 from the upper case 2 to expose the lower case 7, presses the sensor insertion device 1 against the user's body 4, and moves the upper case 2 downward with respect to the lower case 7. Referring to FIG. 4, this pressing causes the sensor base 5 to be remove from the lower case 7 and attached to the body 4. The sensor base 5 has a needle-shaped sensor unit 6 extending downward from the sensor base 5. When the sensor base 5 is attached to the body 4, the sensor unit 6 is inserted into the body 4. A transmitter 8 is attached to the sensor base 5 after the sensor base 5 has been attached to the body 4. The transmitter 8 constitutes a biological information measurement device together with the sensor base 5 and the sensor unit 6, but is not housed in the lower case 7.

Figure 5:
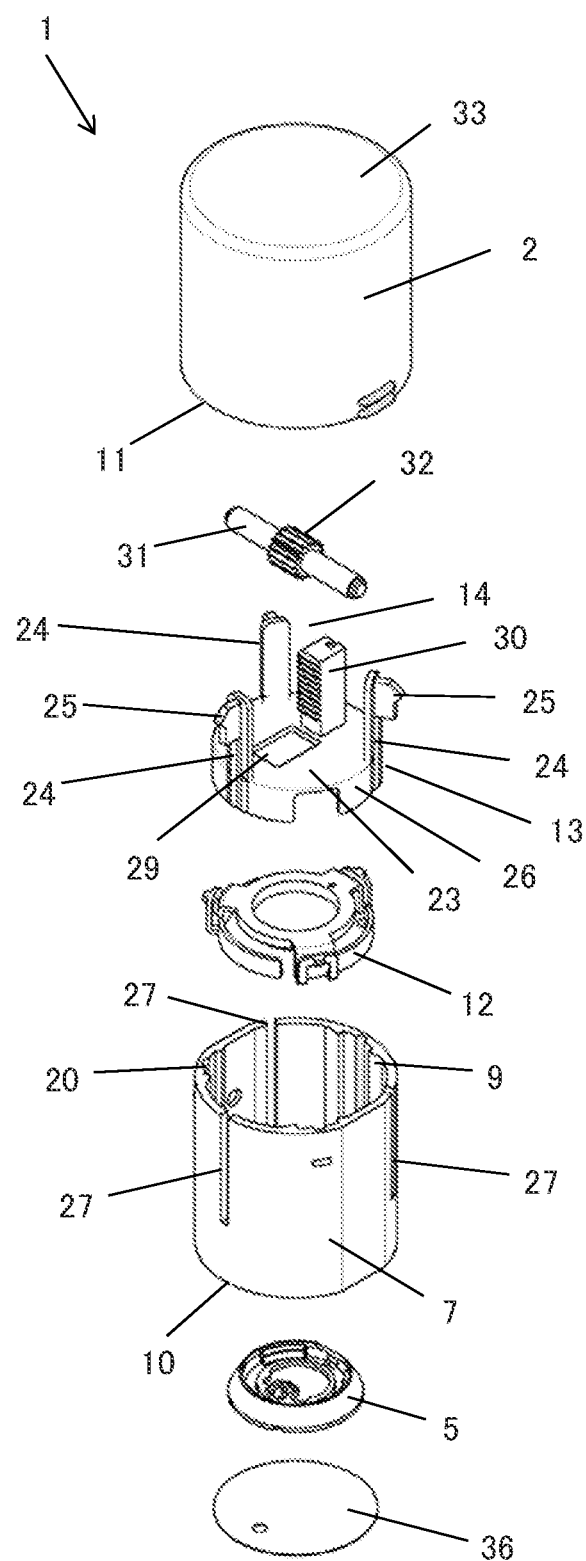
FIG. 5 is an exploded oblique view of the sensor insertion device in FIG. 2.
Figure 6:
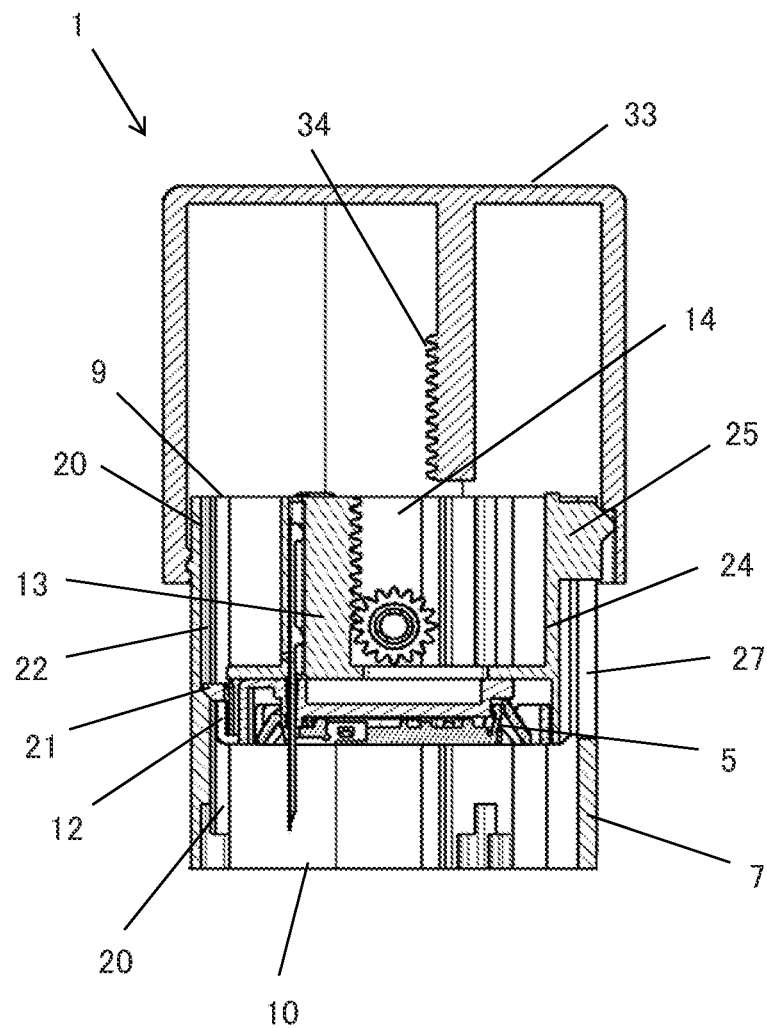
FIG. 6 is a cross-sectional view of the sensor insertion device in FIG. 2.

FIG. 5 is an exploded oblique view of the sensor insertion device 1, and FIG. 6 is a cross-sectional view of the sensor insertion device 1 in the state prior to use. As shown in FIGS. 5 and 6, the sensor insertion device 1 comprises a base holder 12, a needle holder 13, and a needle holder raising mechanism 14 in addition to the above-mentioned upper case 2, lower case 7, and sensor base 5.

The lower case 7 is formed in a cylindrical shape having an upper opening 9 at its upper end and a lower opening 10 at its lower end. The upper case 2 is formed in a cylindrical shape having an opening 11 at its lower end and a closed upper surface. The upper case 2 is covered from above by the outer periphery of the lower case 7, and can move downward with respect to the lower case 7. The upper case 2 and the lower case 7 are disposed coaxially.

The base holder 12 and the needle holder 13 are disposed inside the lower case 7. The base holder 12 and the needle holder 13 constitute a downward moving body that moves downward in the lower case 7 as the upper case 2 moves downward with respect to the lower case 7. The needle holder raising mechanism 14 is disposed inside the lower case 7 and/or the upper case 2. In the illustrated example, the needle holder raising mechanism 14 is disposed inside both cases 2 and 7, but this is only an example. The needle holder 13 is disposed above the base holder 12, and the needle holder raising mechanism 14 is disposed above the needle holder 13.

Figure 7:
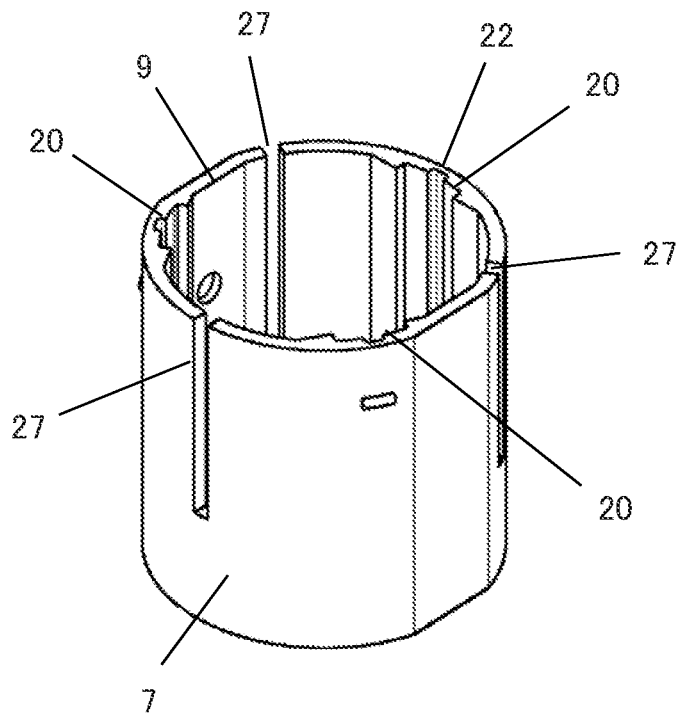
FIG. 7 is an oblique view of the lower case of the sensor insertion device in FIG. 2.
Figure 8:
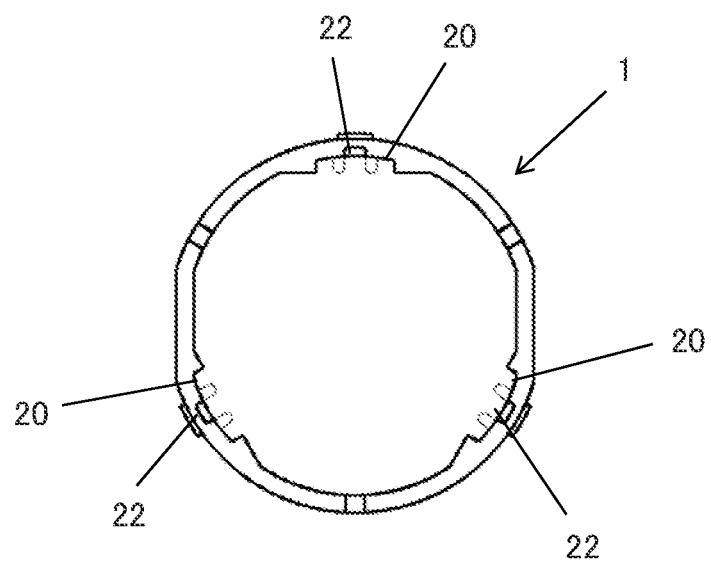
FIG. 8 is a plan view of the lower case of the sensor insertion device in FIG. 2.

FIGS. 7 and 8 show the lower case 7. As shown in FIGS. 5 to 8, the lower case 7 has one or more grooves 20 extending in the up and down direction on its inner peripheral surface. Furthermore, grooves 22 are formed inside the grooves 20. The grooves 20 and 22 extend downward from the upper opening 9 of the lower case 7. The lower case 7 has one or more slits 27 extending downward from the upper opening 9 of the lower case 7. In this embodiment, a plurality of slits 27 are disposed at equal intervals in the circumferential direction, and a plurality of grooves 20 are disposed at equal intervals in the circumferential direction. One of the grooves 20 is formed in the portion of the inner peripheral surface of the lower case 7 that is between slits 27 adjacent to each other in the circumferential direction. One of the slits 27 is formed between grooves 20 adjacent to each other in the circumferential direction.

Figure 9:
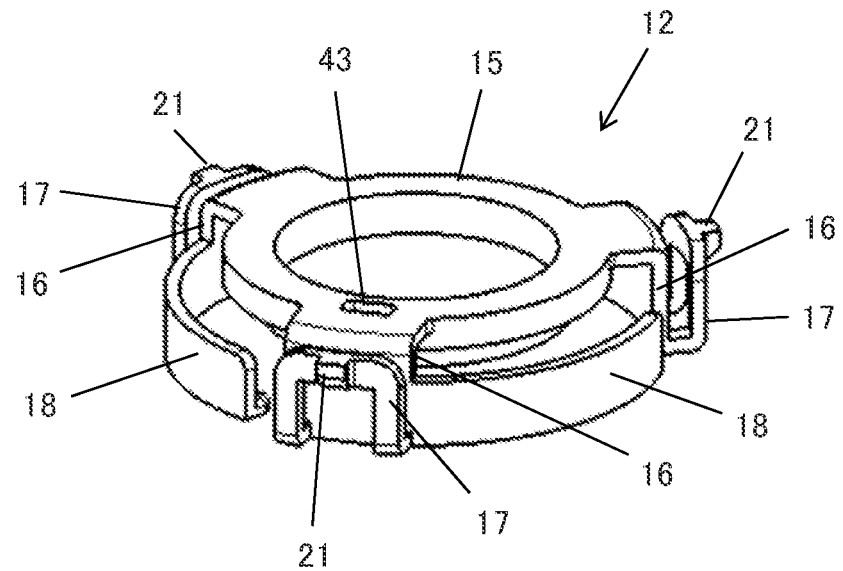
FIG. 9 is an oblique view of the base holder of the sensor insertion device in FIG. 2.
Figure 10:
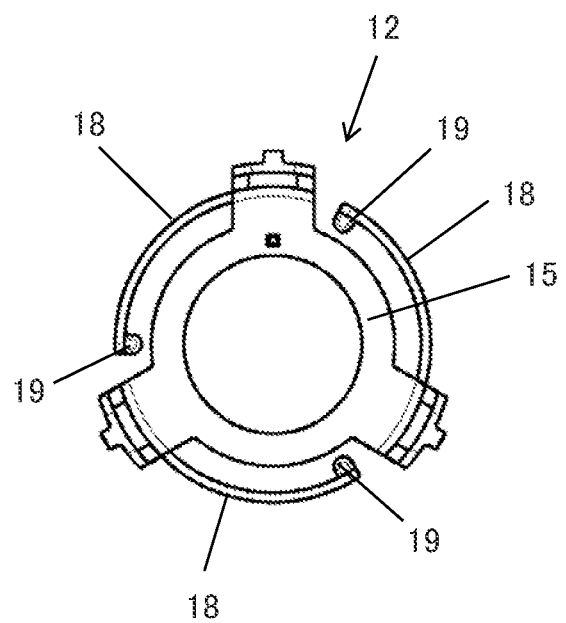
FIG. 10 is a plan view of the base holder of the sensor insertion device in FIG. 2.

FIGS. 9 and 10 show the base holder 12. The base holder 12 has a top plate 15, a plurality of hanging pieces 16, a plurality of engaging pieces 17, a plurality of holding levers 18, a plurality of protrusions 19, and a plurality of protrusions 21. The top plate 15 is formed in an annular shape, for example. The plurality of hanging pieces 16 are disposed on the outer peripheral portion of the top plate 15 at equal intervals in the circumferential direction. The hanging pieces 16 extend downward from the outer peripheral portion of the top plate 15. The engaging pieces 17 and the holding levers 18 are respectively provided to the hanging pieces 16. Each engaging pieces 17 extends outward from the lower end of the corresponding hanging piece 16 and then rises upward. Each holding lever 18 extends in the circumferential direction from the side of the corresponding hanging piece 16. Each holding lever 18 is fixed to the base holder 12 at one end, and is freely displaceable in the inward and outward directions at the other end. The protrusions 19 are respectively provided to the holding levers 18. Each protrusion 19 is provided to the inner peripheral surface of the corresponding holding lever 18 (in particular, the displaceable other end portion). The protrusions 21 are respectively provided to the engaging pieces 17. Each protrusion 21 projects outward from the upper portion of the corresponding engaging piece 17.

Figure 11:
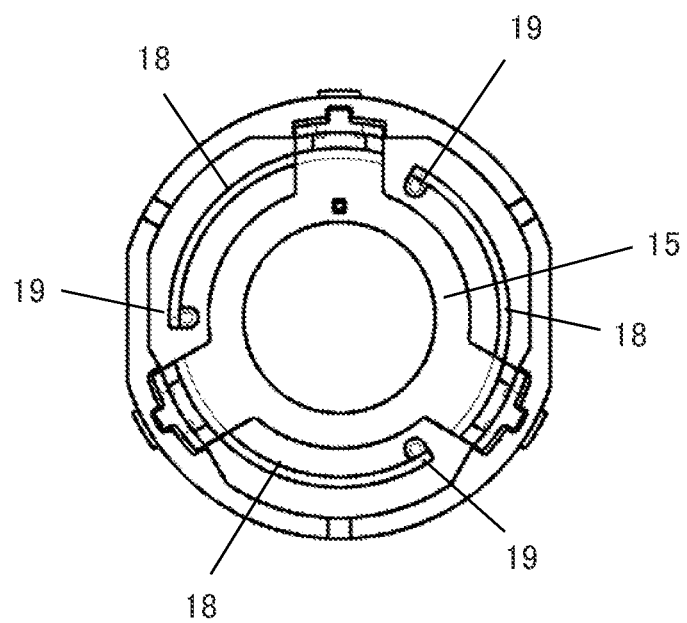
FIG. 11 is a plan view of a state in which the base holder of the sensor insertion device in FIG. 2 has been attached to the lower case.
Figure 12:
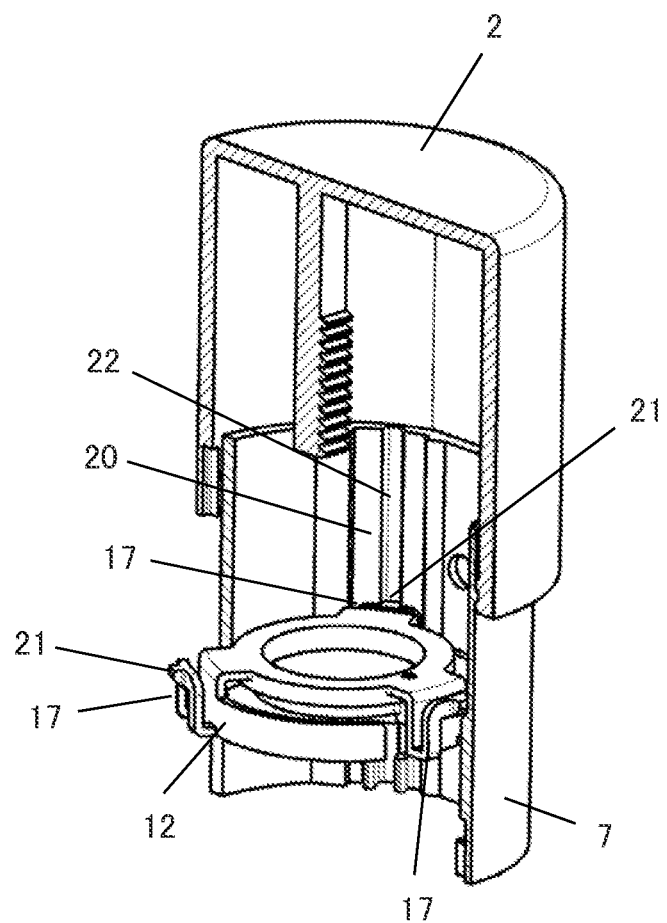
FIG. 12 is an oblique view of the main components, illustrating the state in FIG. 11.
Figure 13:
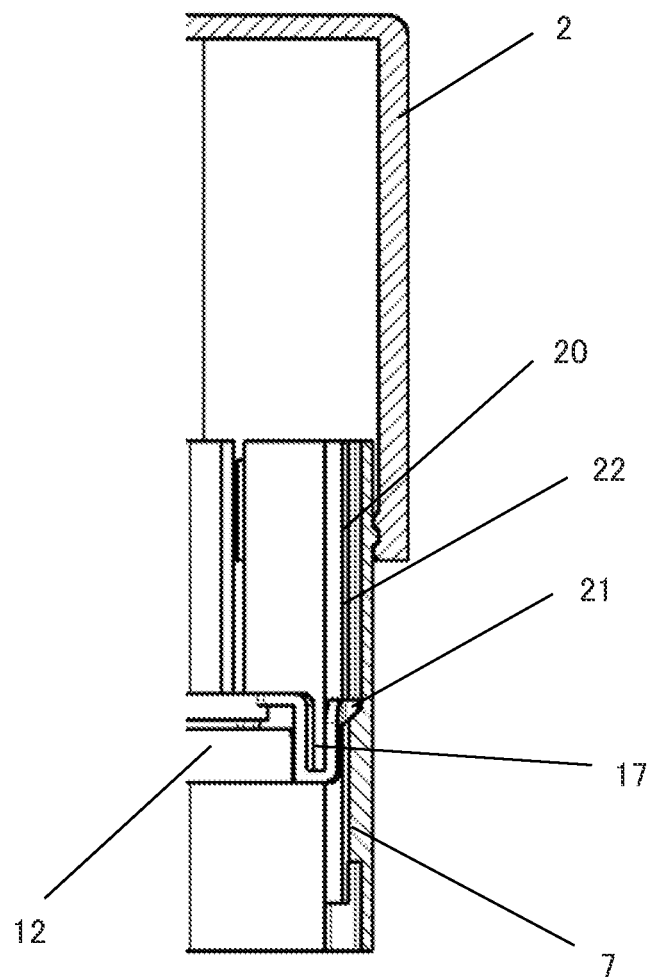
FIG. 13 is a cross-sectional view of the main components, illustrating the state in FIG.

FIGS. 11 to 13 show a state in which the base holder 12 has been attached to the lower case 7. In mounting the base holder 12 on the lower case 7, the base holder 12 is inserted into the lower case 7 through the upper opening 9. The engaging pieces 17 are engaged with the grooves 20, and the protrusions 21 are engaged with the grooves 22. The base holder 12 is guided by the grooves 20 and 22 and moves downward in the lower case 7. The lower ends of the grooves 22 are located above the lower ends of the grooves 20. Therefore, when the protrusions 21 hit with the lower ends of the grooves 22, the downward movement of the lower case 7 stops. At the time of attachment, that is, in the state prior to use, the base holder 12 is temporarily held in the lower case 7 at a standby position set in a middle portion in the lengthwise direction of the lower case 7.

Figure 14:
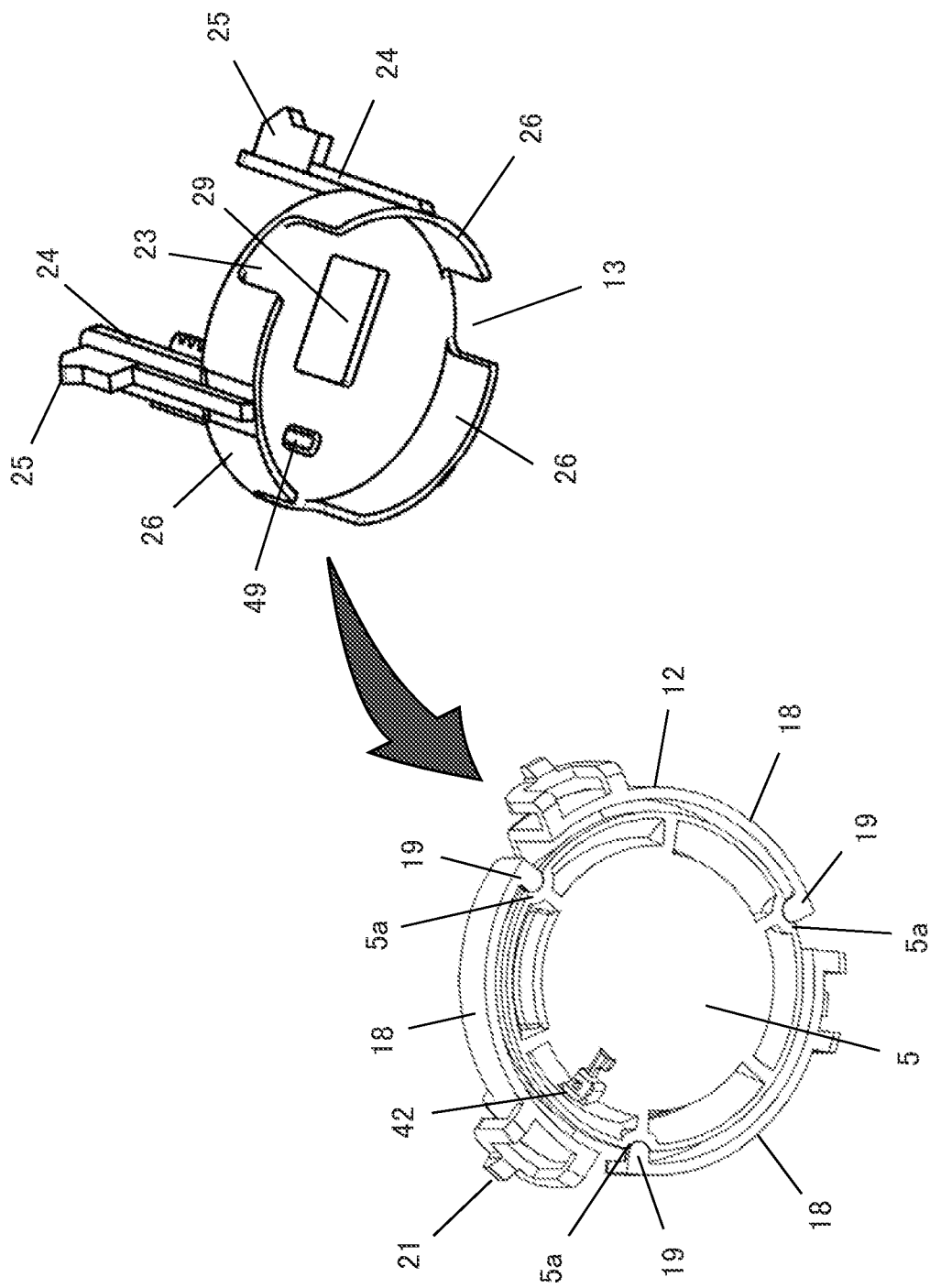
FIG. 14 is an oblique view showing a state in which the sensor base is held by the base holder of the sensor insertion device in FIG. 2, and a needle holder.
Figure 15:
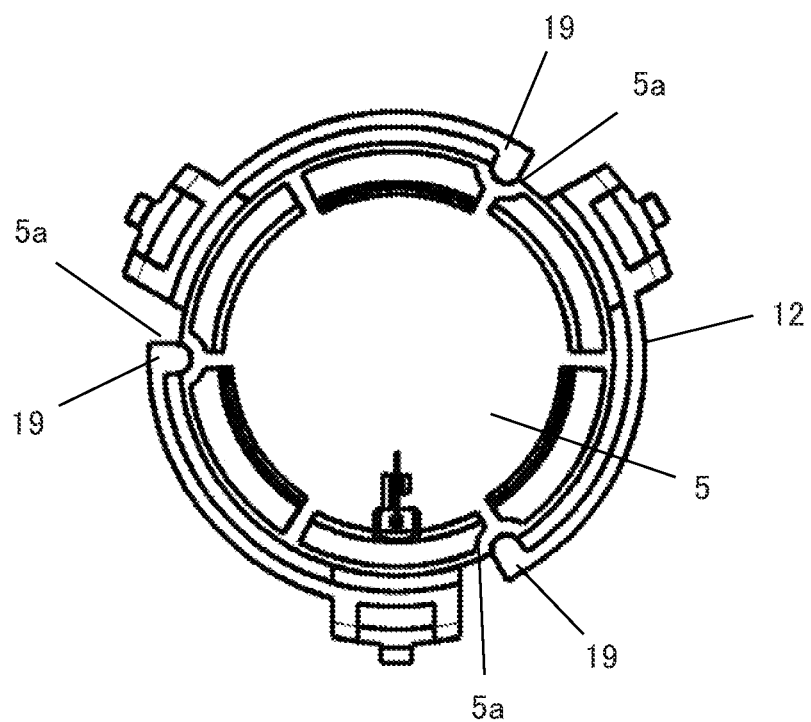
FIG. 15 is a bottom view of the base holder and sensor base in FIG. 14 as viewed from below.

FIGS. 14 and 15 show the base holder 12 in a state of being assembled with the sensor base 5. As shown in FIGS. 6, 14, and 15, the sensor base 5 is pushed into the base holder 12 from below. The top plate 15 is positioned above the sensor base 5, and the hanging pieces 16 and the holding levers 18 are positioned on the outer periphery of the sensor base 5. Recesses 5a are provided to the outer peripheral portion of the sensor base 5 (see also FIG. 4). The sensor base 5 is held inside the base holder 12 when the protrusions 19 engage with the recesses 5a. Thus, at the point when the base holder 12 is attached to the lower case 7, the sensor base 5 is pre-held in the base holder 12 and is pre-housed in the lower case 7. At the stage of actually using the sensor insertion device 1, there is no need to attach the sensor base 5 to the sensor insertion device 1.

As shown in FIGS. 5, 6, and 14, the needle holder 13 has a top plate 23, a plurality of risers 24, a plurality of protrusions 25, and a plurality of restraining walls 26. The top plate 23 is formed in a substantially disk shape, for example. The risers 24 are disposed on the outer peripheral portion of the top plate 23 at equal intervals in the circumferential direction. Each riser 24 extends upward from the top plate 23. The protrusions 25 are respectively provided to the risers 24. Each protrusion 25 protrudes outward from the upper part of the corresponding riser 24. The restraining walls 26 hang downward from the top plate 23.

In attaching the needle holder 13 to the lower case 7, the needle holder 13 is inserted into the lower case 7 through the upper opening 9. The protrusions 25 are engaged with the slits 27. The needle holder 13 is guided by the slits 27 and moves downward in the lower case 7. When the needle holder 13 hits the upper surface of the base holder 12 and the protrusions 21 of the base holder 12 hit the lower ends of the grooves 22, the downward movement of the needle holder 13 also stops. As a result, the needle holder 13 is mounted on the base holder 12 and is temporarily held along with the base holder 12 in the lower case 7. The protrusions 21 and the grooves 22 constitute a standby position setting unit that holds the base holder 12 and the needle holder 13 in a standby position at the time of mounting, that is, prior to use. When the needle holder 13 is being held in the standby position, the protrusions 25 are located at the upper part of the slits 27.

Figure 16:
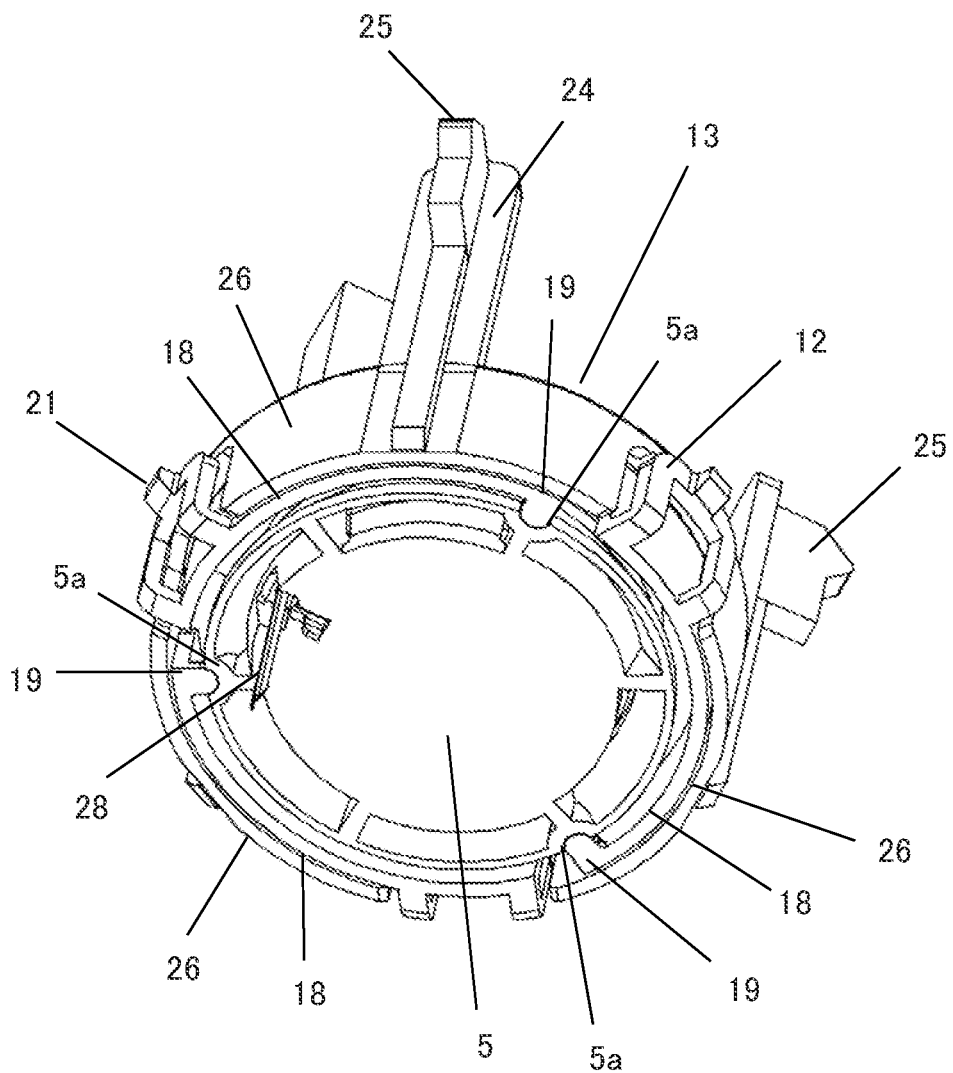
FIG. 16 is an oblique view showing a state in which the needle holder in FIG. 14 has been attached to the base holder.
Figure 17:
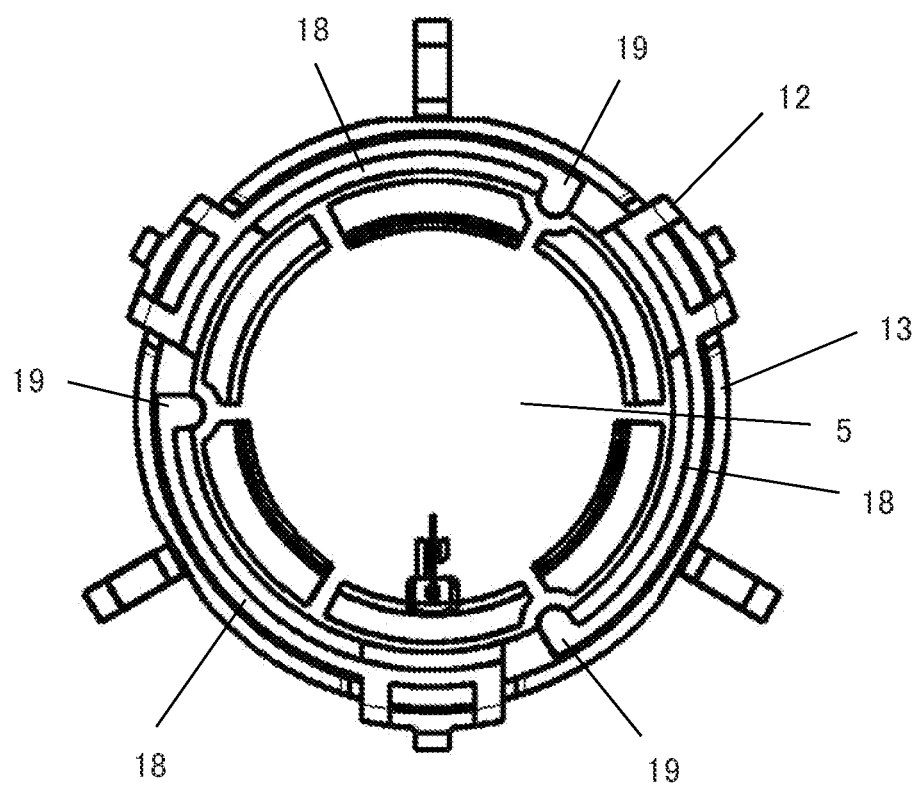
FIG. 17 is a bottom view of the state in FIG. 16 as viewed from below.

FIGS. 16 and 17 show a state in which the needle holder 13 has been mounted on the base holder 12. As shown in FIGS. 16 and 17, when the needle holder 13 is mounted on the base holder 12, the restraining walls 26 are disposed on the outer periphery of the holding levers 18, and the holding levers 18 cannot be displaced outward. As a result, the protrusions 19 are held in a state of being engaged with the recesses 5a of the sensor base 5. This prevents the sensor base 5 from accidentally falling downward.

The needle holder 13 holds the guide needle 28. In the state prior to use, the guide needle 28 extends downward from the needle holder 13 and is inserted into the base holder 12 and the sensor base 5 to include the sensor unit 6. The shape of the guide needle 28 and the structure so that the guide needle 28 will include the sensor unit 6 will be described below with reference to FIG. 27 and so forth.

As shown in FIGS. 5 and 6, the needle holder 13 has an opening 29 formed in the top plate 23. The needle holder 13 has a rack 30 that is raised upward from the top plate 23 at a position adjacent to the opening 29. The rack 30 meshes with a pinion 32. The pinion 32 is provided on a rotating shaft 31 rotatably supported by the lower case 7. The rotating shaft 31 is oriented horizontally in the lower case 7 and is disposed higher than the (top plate 23 of the) needle holder 13.

Figure 18:
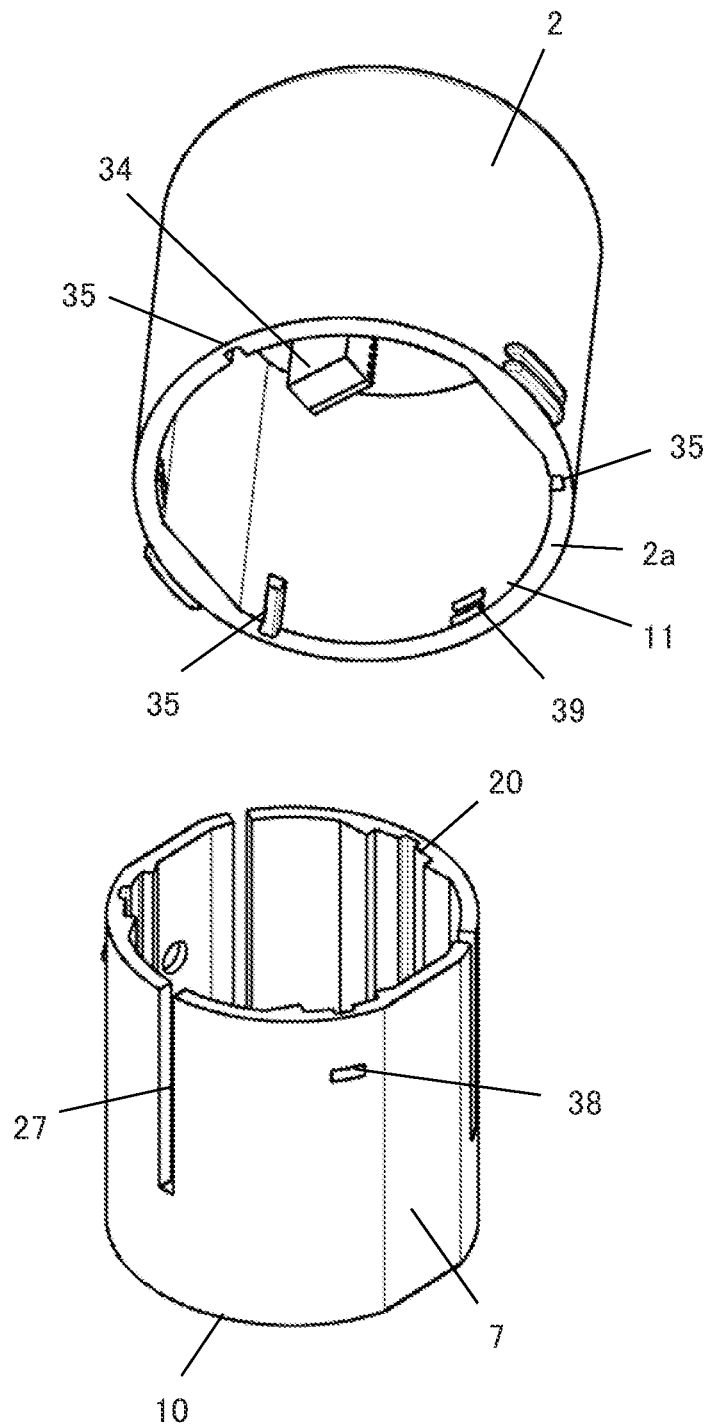
FIG. 18 is an exploded oblique view of the lower case and the upper case of the sensor insertion device in FIG. 2.

FIG. 18 is an exploded oblique view of the upper case 2 and the lower case 7. As shown in FIGS. 5, 6, and 18, the upper case 2 has a top plate 33 that forms the upper surface. The upper case 2 has a rack 34 that is disposed in the upper case 2, extending downward from the lower surface of the top plate 33. The needle holder raising mechanism 14 is constituted by these racks 30 and 34 and the pinion 32. The rack 30 and the rack 34 are disposed so as to face each other in the radial direction of the rotating shaft 31 with the pinion 32 in between (see also FIGS. 19 to 22). In a state in which the upper case 2 is assembled to the lower case 7, the rack 34 is positioned so as to overlap the opening 29 in plan view (see FIG. 19).

As shown in FIG. 18, the upper case 2 has a plurality of engaging portions 35 and protrusions 39. The engaging portions 35 are provided to the lower part of the inner peripheral surface of the upper case 2, and are disposed at equal intervals in the circumferential direction. In this embodiment, each engaging portion 35 is constituted by a groove extending upward from the opening 11 on the inner peripheral surface of the upper case 2. The two protrusions 39 are provided one above the other on the inner peripheral surface near the opening 11. A recess is formed between the two protrusions 39. Meanwhile, the lower case 7 has protrusions 38 provided on its outer peripheral surface. The protrusions 38 are provided between the slits 27 at the upper part of the lower case 7. The portion of the peripheral wall of the lower case 7 where the protrusions 38 are disposed can flex in and out. The slits 27 extend downward from the opening 11 and terminate at a middle portion of the lower case 7 in the lengthwise direction. The portions of the slits 27 above the lower ends can flex, while the portions below the lower ends of the slits 27 are more resistant to flexing.

The upper case 2 is attached to the lower case 7 in a state in which the base holder 12 and the needle holder 13 are being held in a standby state. First, the protrusions 25 of the needle holder 13 are engaged with the engaging portions 35. When the opening 11 is covered by the upper opening 9 and the upper case 2 is pushed in, the lower of the two protrusions 39 hits the protrusions 38, and the peripheral wall of the lower case 7 flexes inward due to a wedge action. When the lower of the two protrusions 39 rides up and over the protrusions 38 and moves downward, the peripheral wall of the lower case 7 is restored to its former state, and the protrusions 38 are latched in the recess between the two protrusions 39 (see FIG. 24). This completes the attachment of the upper case 2 to the lower case 7, and the upper case 2 is held at a specific upper position. The protrusions 38 constitute an upper position setting unit for holding the upper case 2 in the upper position. The two protrusions 39 are provided so as to protrude in the inner peripheral direction from each of the upper and lower portions of the protrusions 38 in a state in which the upper case 2 is held in the upper position.

Figure 24:
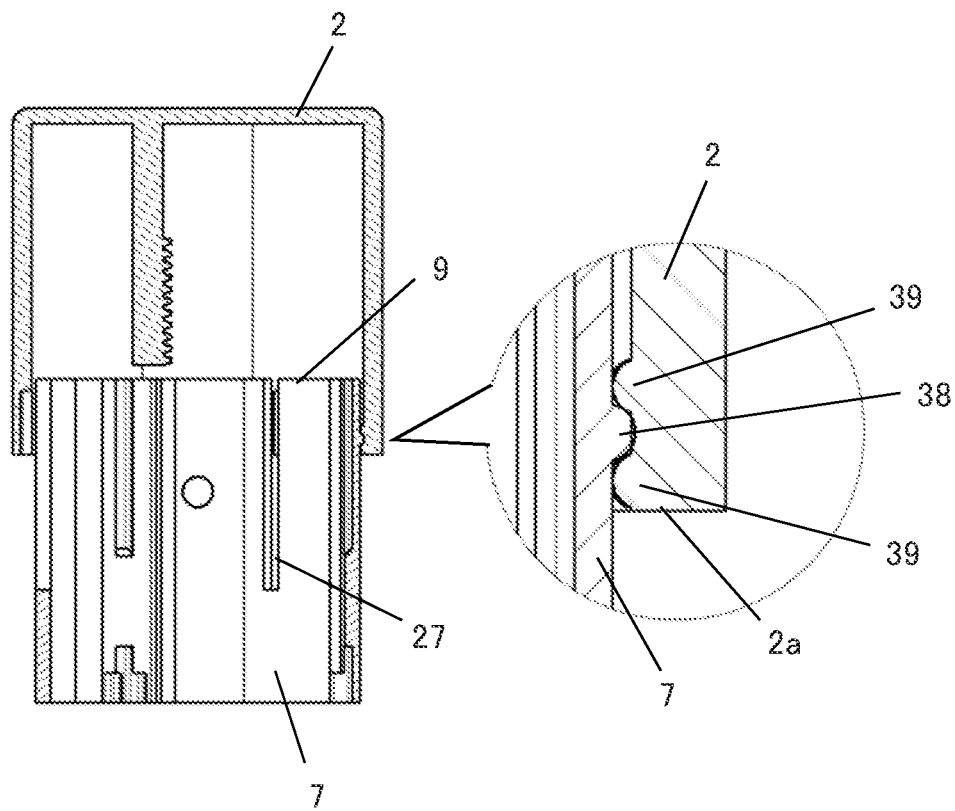
FIG. 24 is a cross-sectional view showing the relation between the lower case and the upper case of the sensor insertion device in FIG. 2.
Figure 25:
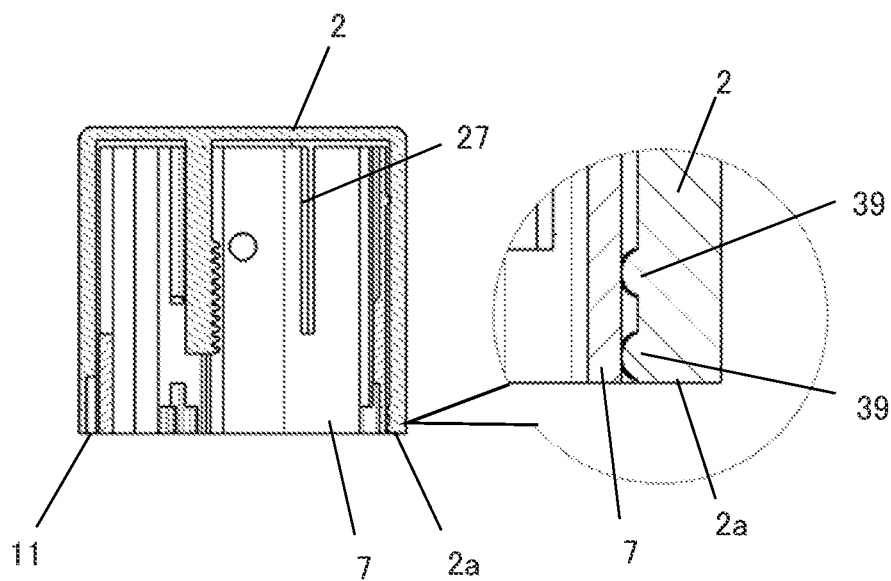
FIG. 25 is a cross-sectional view showing the relation between the lower case and the upper case of the sensor insertion device in FIG. 2.

FIGS. 19 to 22 show the operation when the sensor insertion device 1 is used. FIG. 23 is an oblique view of a used sensor insertion device 1. FIGS. 24 and 25 show detail views of the upper case 2 and the lower case 7, with FIG. 24 corresponding to FIG. 19, and FIG. 25 corresponding to FIG. 21.

Figure 19:
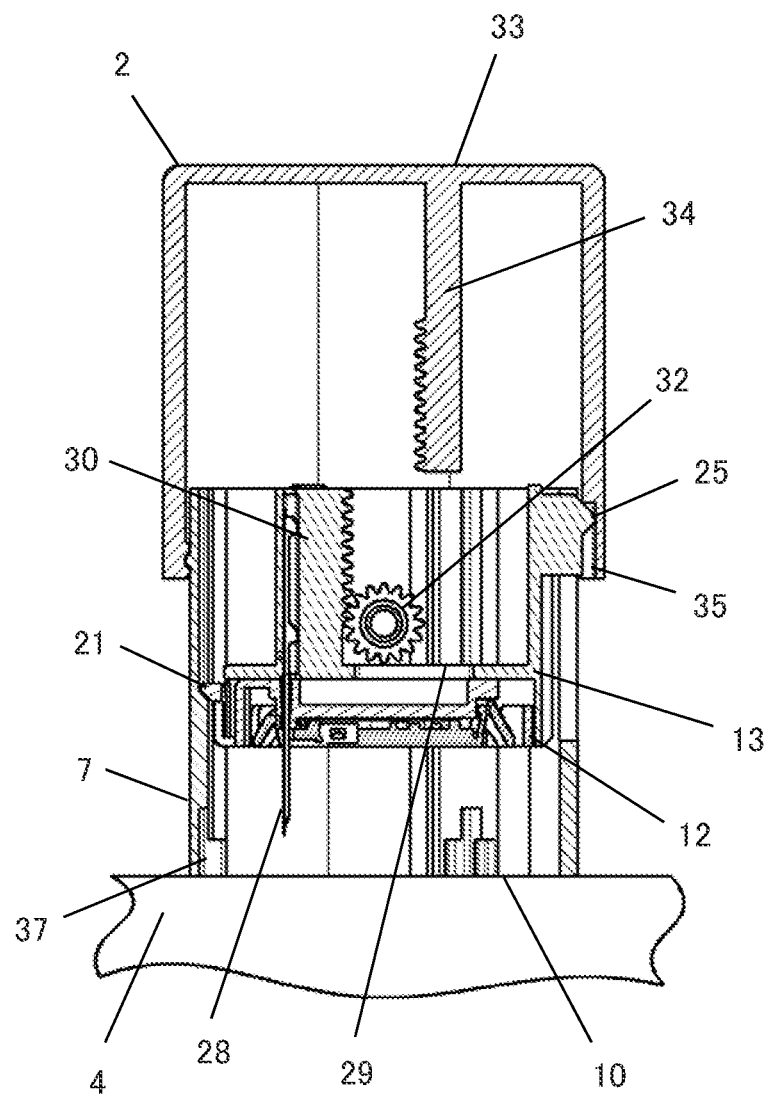
FIG. 19 is a cross-sectional view of the operating state of the sensor insertion device in FIG. 2.

As shown in FIGS. 19 and 24, in using the sensor insertion device 1, the lower opening 10 of the lower case 7 is brought into contact with the skin of the user's body 4. At this point, the base holder 12 and the needle holder 13 are held in the standby position, and the guide needle 28 is housed inside the cases 2 and 7, away from (above) the skin.

Next, the upper case 2 is pushed down with respect to the lower case 7. The protrusions 25 of the needle holder 13 are engaged with the engaging portions 35 of the upper case 2 through the slits 27. More precisely, the protrusions 25 are brought into contact with the upper ends of the groove-shaped engaging portions 35. Therefore, when the upper case 2 is pushed down, the protrusions 25 are pushed downward by the upper case 2, and the pressing force is transmitted through the needle holder 13 to the base holder 12. If the pressing force is strong enough, the hold of the upper case 2 by the upper position setting unit is released by wedge action, and the hold of the standby state by the standby position setting unit is also released.

Figure 20:
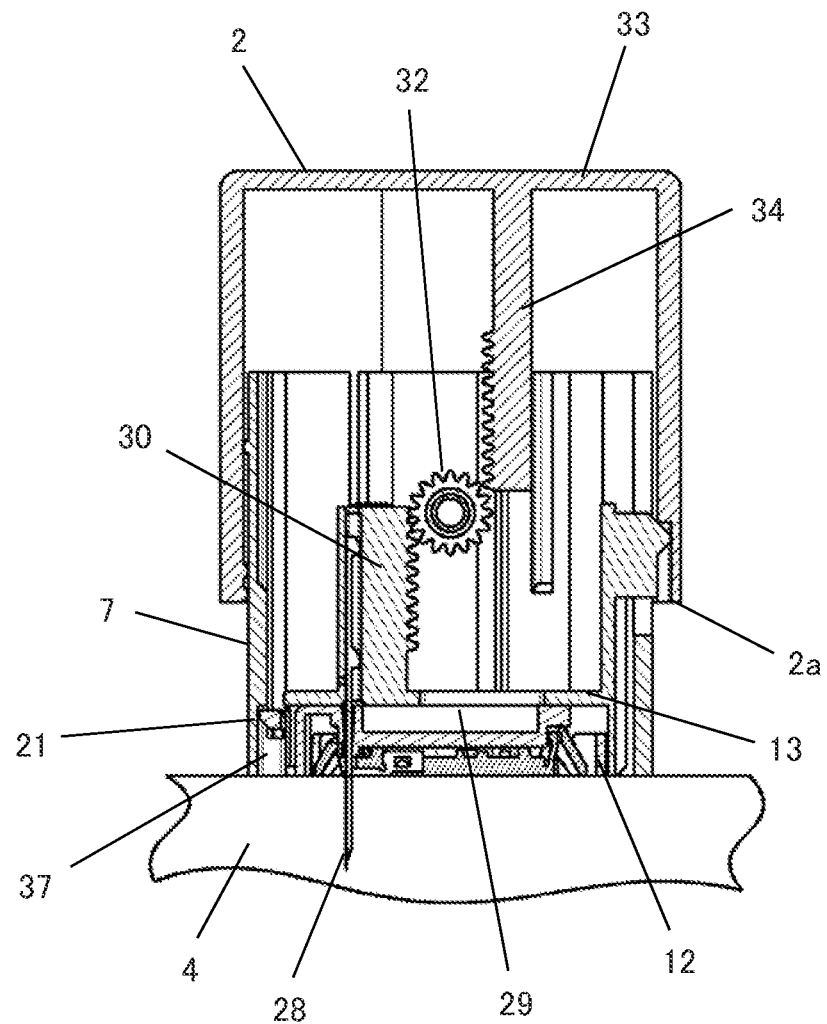
FIG. 20 is a cross-sectional view of the operating state of the sensor insertion device in FIG. 2.

As shown in FIG. 20, the upper case 2 moves downward from the upper position with respect to the lower case 7, and the base holder 12 and the needle holder 13 are pushed by the upper case 2 and move downward from the standby position. The protrusions 25 slide downward in the slits 27, and the downward motion of the needle holder 13 is guided by the slits 27. At this point, the rack 30 moves downward with respect to the pinion 32, and the pinion 32 and the rotating shaft 31 rotate in one direction (the counterclockwise direction in FIG. 19). Also, the engaging pieces 17 slide downward in the grooves 20, and the downward motion of the base holder 12 is guided by the grooves 20. The grooves 20 extend further to the lower side of the lower case 7 than the slits 27. Therefore, the base holder 12 can move to the opening 10 of the lower case 7.

The lower case 7 has a plurality of engaging portions 37. Each engaging portion 37 is provided in a concave shape at the lower end portion of the corresponding groove 20. When the base holder 12 reaches the vicinity of the lower opening 10, the protrusions 21 are forced into the corresponding engaging portions 37, resulting in engagement. Even if the base holder 12 tries to move upward, the protrusions 21 will hit the upper ends of the engaging portions 37, so this upward motion is restricted.

When the base holder 12 moves to the opening 10, the guide needle 28 and the sensor unit 6 contained therein are inserted into the body 4, and the lower surface of the sensor base 5 comes into contact with the body 4. A skin tape 36 (see FIG. 5) is provided on the lower surface of the sensor base 5. The sensor base 5 is attached to the body 4 by the adhesion of the skin tape 36.

When the sensor base 5 comes into contact with the body 4, the opening 11 of the upper case 2 is located above the lower opening 10 of the lower case 7. In view of this, the upper case 2 is further pushed down with respect to the lower case 7. If the pressing force is sufficient, the protrusions 25 and the engaging portions are disengaged, the upper case 2 moves downward, and the lower end of the rack 34 is engaged with the pinion 32. After this, the needle holder raising mechanism 14 comes into play. The rack 34 moves downward with respect to the pinion 32 in a state of being meshed with the pinion 32, and the pinion 32 is rotationally driven in the opposite direction (the clockwise direction in FIG. 20). Consequently, the rack 30 is moved in the opposite direction, that is, upward. The base holder 12 and the sensor base 5 remain unmoved with respect to the lower case 7, while the upper case 2 moves downward with respect to the lower case 7 and the needle holder 13 rises away from the base holder 12 in the lower case 7. The guide needle 28 rises together with the needle holder 13, is pulled out of the body 4, and is pulled up above the base holder 12. The rack 34 is inserted into the opening 29 formed in the top plate 33 of the needle holder 13, and the downward movement of the upper case 2 and the upward movement of the needle holder 13 are not hindered.

Figure 21:
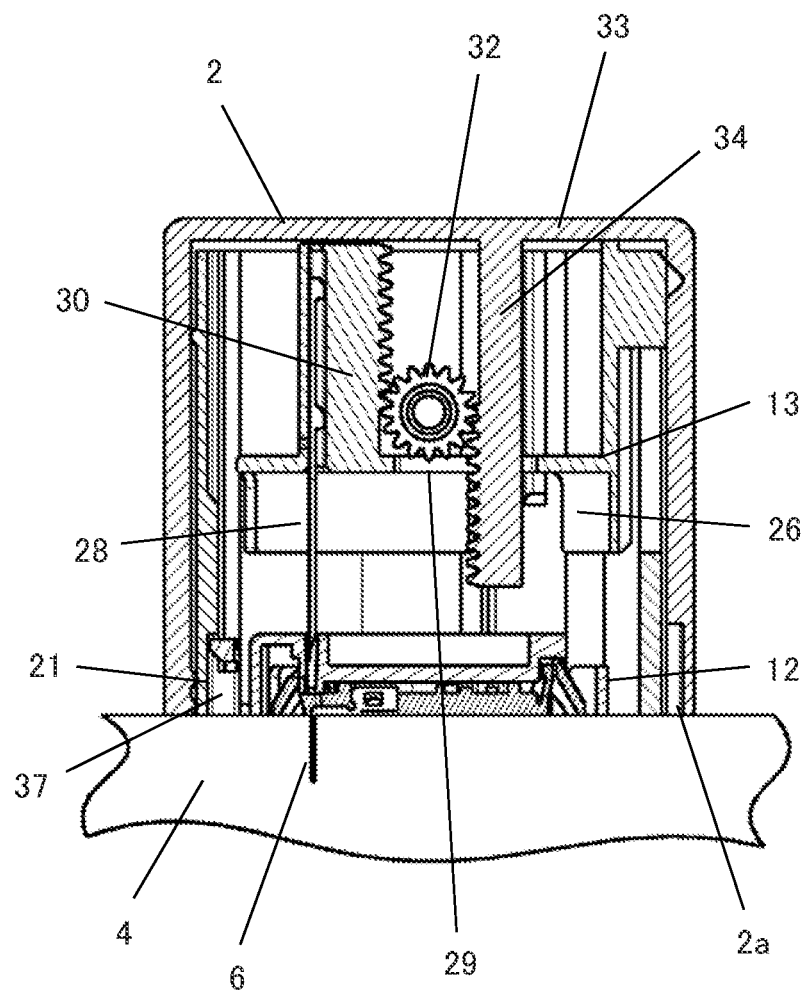
FIG. 21 is a cross-sectional view of the operating state of the sensor insertion device in FIG. 2.

As shown in FIGS. 21 and 25, the upper case 2 is pushed down until the opening 11 is at substantially the same position as the lower opening 10. The upper case 2 has a skin contact portion 2a that comes into contact with the skin of the body 4. The skin contact portion 2a is formed on the opening edge of the opening 11, or in other words, on the portion of the lower end of the upper case 2 that faces the body 4. The upper case 2 is pushed down until the skin contact portion 2a comes into contact with the skin. When the upper case 2 is properly pushed down in this way, the guide needle 28 is pulled up into the lower case 7, and the guide needle 28 is covered from below by the base holder 12. The lower case 7 is in a state of being completely housed within the upper case 2.

The sensor insertion device 1 also comprises a holding mechanism for holding the upper case 2 on the lower case 7 in a state in which the upper case 2 has been pushed down until the skin contact portion 2a comes into contact with the skin. The protrusions 39 of the upper case 2 are pressed against the lower end of the outer peripheral surface of the lower case 7 as the upper case 2 moves downward from the upper position with respect to the lower case 7. Since the lower end of the peripheral wall of the lower case 7 is lower than the lower end of the slit 27, this pressing can be withstood with almost no deformation. Consequently, the protrusions 39 of the upper case 2 and the portion of the lower case 7 that engages with the protrusions 39 constitute a holding mechanism for holding the upper case 2 on the lower case 7.

Figure 26:
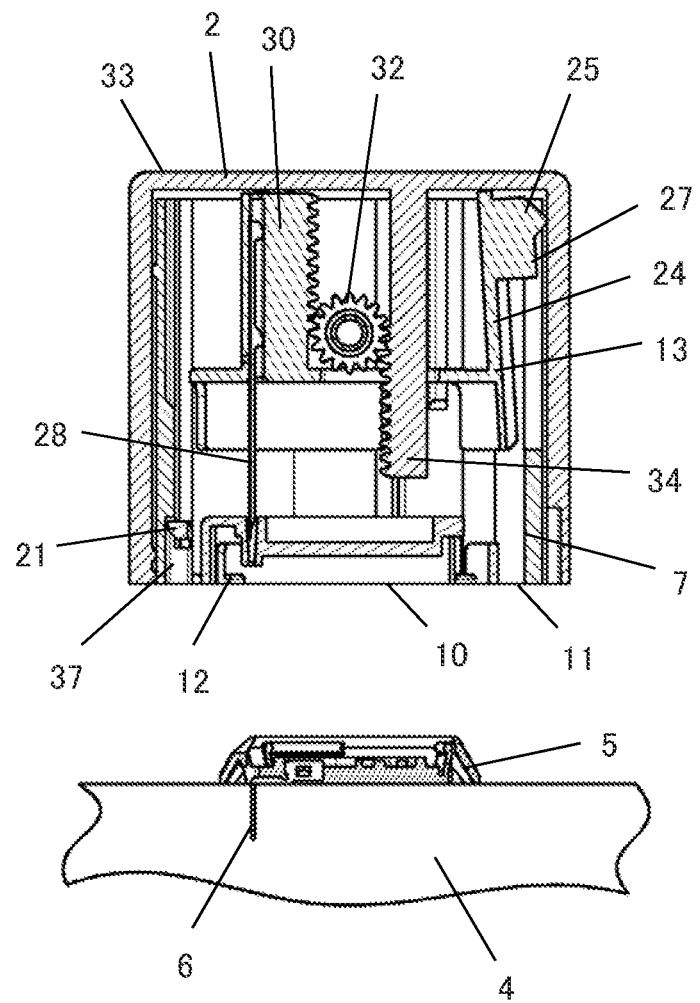
FIG. 26 is a cross-sectional view showing an example of the holding mechanism of the sensor insertion device in FIG. 2.
Figure 27:
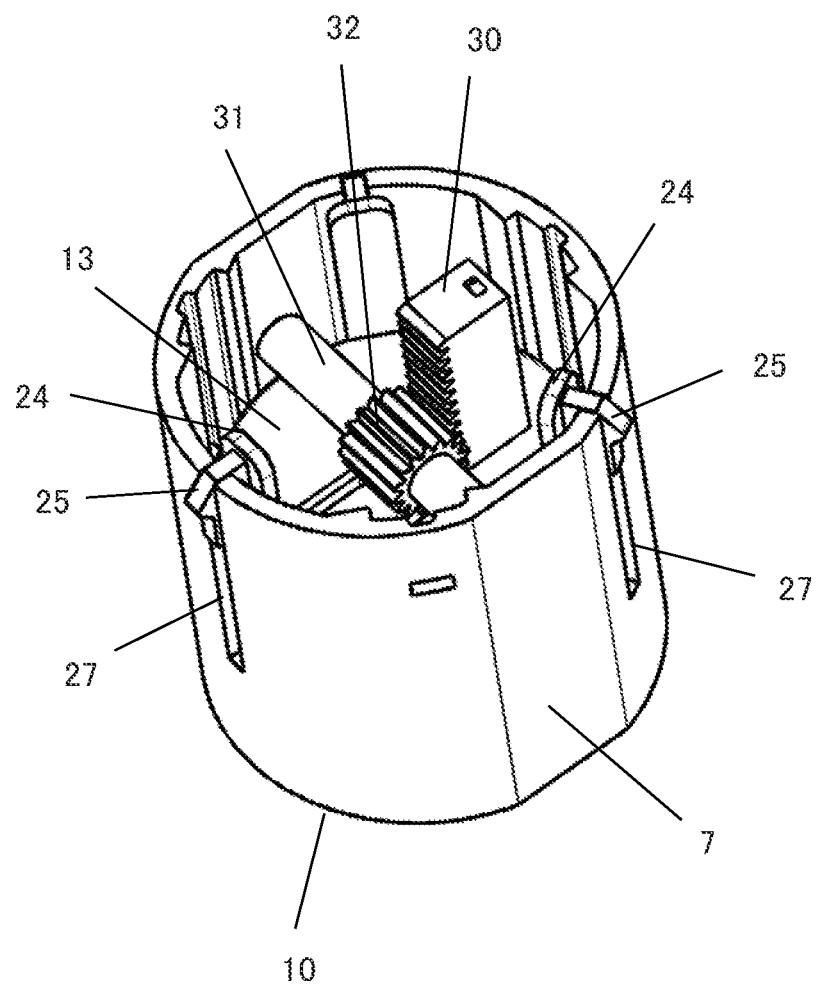
FIG. 27 is an oblique view of the lower case, illustrating the state in FIG. 26.

Furthermore, as shown in FIGS. 26 and 27, the protrusions 25 of the needle holder 13 can also contribute to holding. When the upper case 2 is pushed down, the protrusions 25 of the needle holder 13 are pushed from the upper end of the engaging portions 35 of the upper case 2, and the needle holder 13 moves downward. While the upper case 2 is being pushed down, the needle holder 13 begins to rise, at which point the protrusions 25 and the engaging portions 35 are disengaged. The risers 24 are elastically deformed inward, and the protrusions 25 engage with the inner peripheral surface of the upper case 2 under the elastic force of the risers 24. When the skin contact portion 2a is in contact with the skin, the protrusions 25 engage with the upper end portion of the inner peripheral surface of the upper case 2. The needle holder 13 is engaged with the lower case 7 via the rack 30, the pinion 32, and the rotating shaft 31. Consequently, the protrusions 25 of the needle holder 13 and the portion of the upper case 2 that engages with the protrusions 25 also constitute a holding mechanism for holding the upper case 2 on the lower case 7.

Thus, the protrusions constituting the holding mechanism need not be provided to the upper case 2 or the lower case 7 itself, and may instead be provided to a member that is engaged with the upper case 2 or the lower case 7. Also, the holding mechanism may be constituted by protrusions provided on the outer peripheral surface of the lower case 7 and engaging portions that are provided on the inner peripheral surface of the upper case 2 and engage with these protrusions.

As the needle holder 13 rises, the restraining walls 26 of the needle holder 13 rise away from the holding levers 18 of the base holder 12, and the other ends of the holding levers 18 can be displaced outward. Therefore, the protrusions 19 move away from the recesses 5a in the sensor base 5, and the sensor base 5 is released from the base holder 12.

Figure 22:
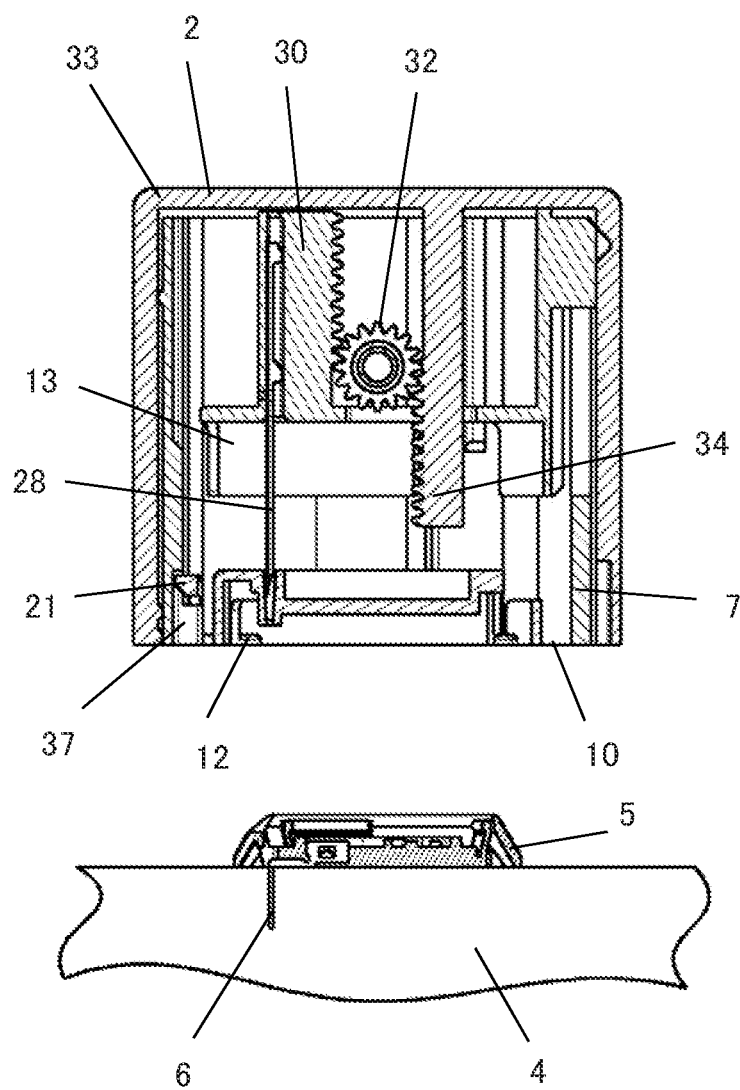
FIG. 22 is a cross-sectional view of the operating state of the sensor insertion device in FIG. 2.
Figure 23:
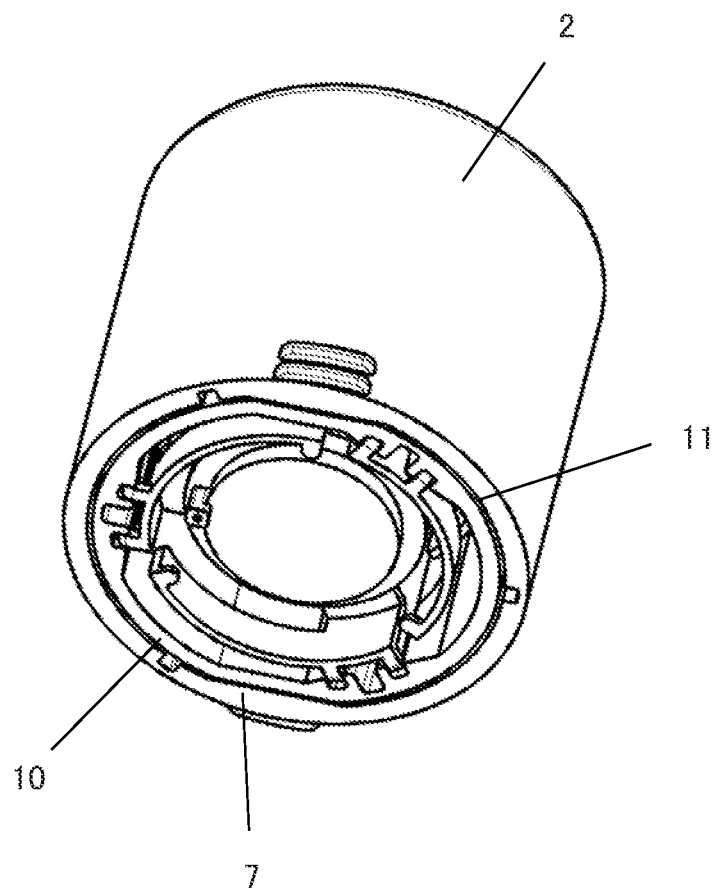
FIG. 23 is an oblique view showing the used state of the sensor insertion device in FIG. 2.

As shown in FIGS. 22 and 23, when the pressing of the upper case 2 is completed and the sensor insertion device 1 is lifted upward from the body 4, the sensor base 5 remains attached to the body 4. Meanwhile, the base holder 12 covers the lower opening 10 of the lower case 7. The guide needle 28 is housed inside the cases 2 and 7, is hidden by the base holder 12, and is in an unexposed state. This prevents the guide needle 28 from touching the user's hand, and ensures that a used sensor insertion device 1 will be safe.

Furthermore, the upper case 2 is held on the lower case 7 in a state in which the opening 11 of the upper case 2 is at substantially the same position as the lower opening 10 of the lower case 7, or in other words, a state in which the lower case 7 is completely housed in the upper case 2. The user can thus look at the sensor insertion device 1 held in this way and can tell at a glance that the device has been used. As a result, the user will not attempt to use the sensor insertion device 1 again, which makes the work much more efficient.

In this embodiment, the lower case 7 is provided with the slits 27. Since a movable portion is provided to the lower case 7, the upper case 2 can be more rigid. The user can firmly grasp the upper case 2. Also, the cylindrical portion of the upper case 2 is thicker than the cylindrical portion of the lower case 7 (see FIG. 23). This also provides greater rigidity to the upper case 2.

In the above example, there were three each of the elements 16 to 22, 24 to 27, 35, and 37, but there is no particular restriction on the number of these elements.

Figure 28:
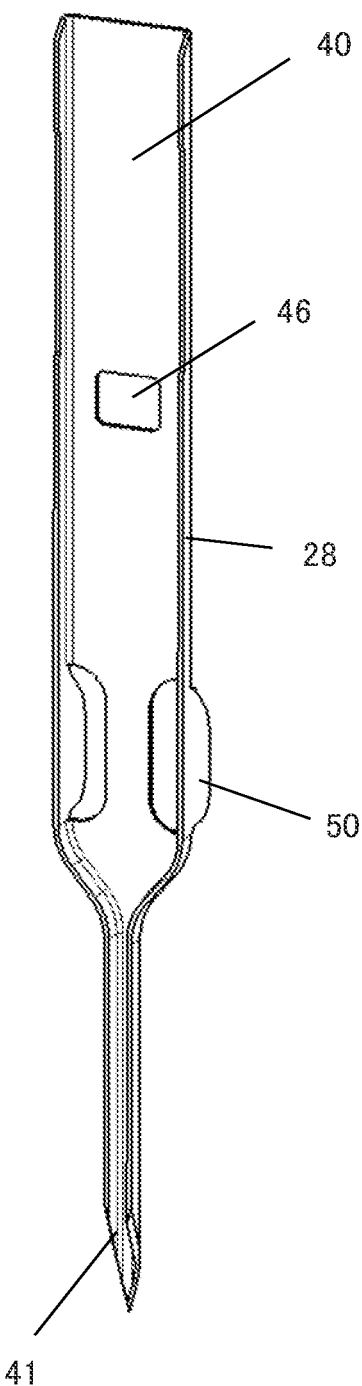
FIG. 28 is an oblique view of the guide needle of the sensor insertion device in FIG. 2.
Figure 29:
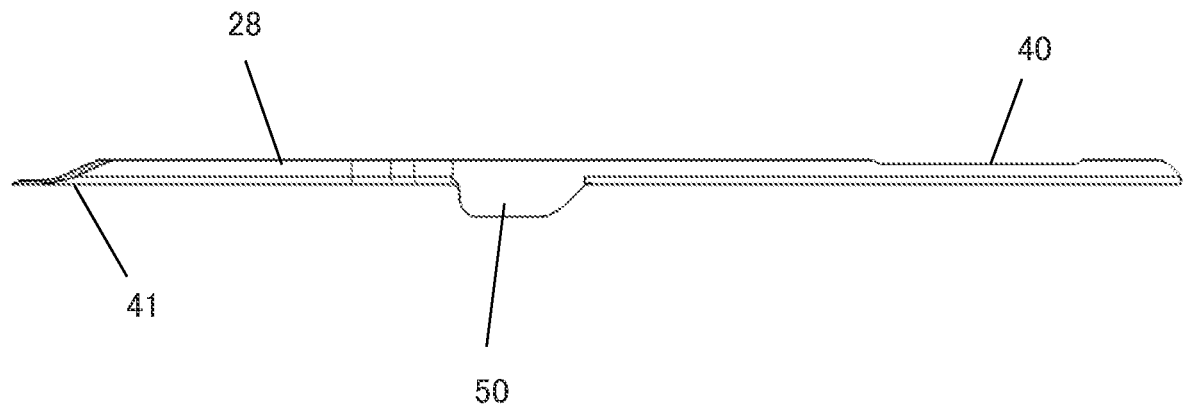
FIG. 29 is a front view of the guide needle of the sensor insertion device in FIG. 2.
Figure 30:
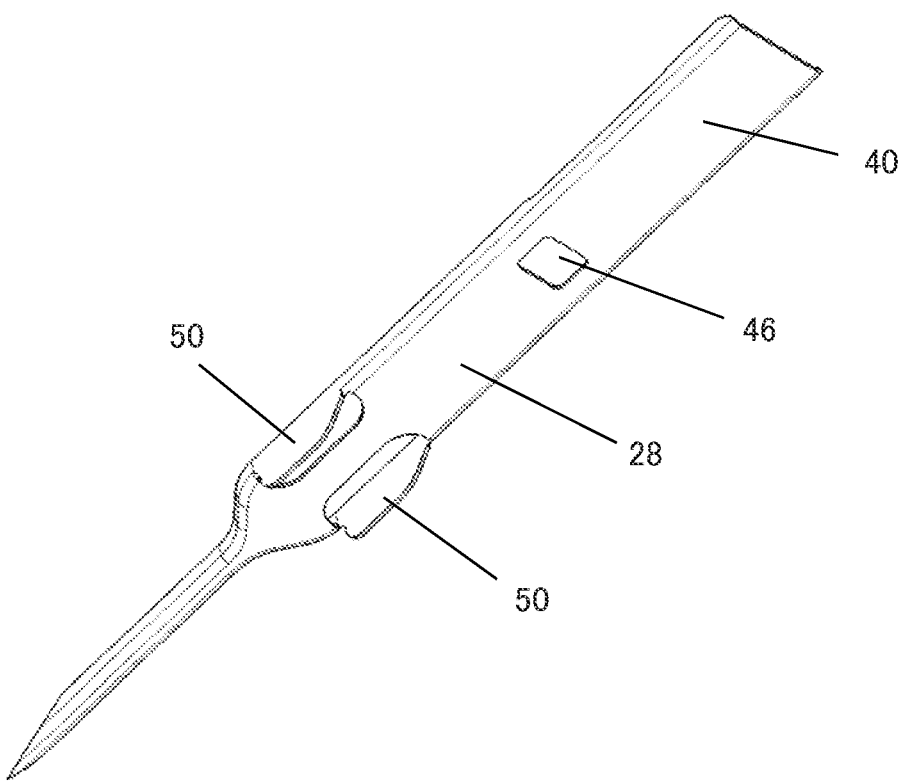
FIG. 30 is an oblique view of the guide needle of the sensor insertion device in FIG. 2.

Next, the guide needle 28 will be described with reference to FIGS. 28 to 49. FIGS. 28 to 30 show the guide needle 28. The guide needle 28 is formed, for example, by working a single sheet of material. The guide needle 28 has an attachment portion 40 and a body insertion portion 41. The attachment portion 40 is formed at the upper portion of the guide needle 28, and the body insertion portion 41 is formed at the lower portion of the guide needle 28.

FIGS. 31 to 34 show the procedure for mounting the guide needle 28. First, the guide needle 28 is held in an upright orientation by a holding jig (not shown). The guide needle 28 is inserted into a first through-hole 42 in the sensor base 5 (see FIGS. 31, 35, and 36). At this point, the sensor unit 6 is included in the guide needle 28. This inclusion will be described below.

Figure 32:
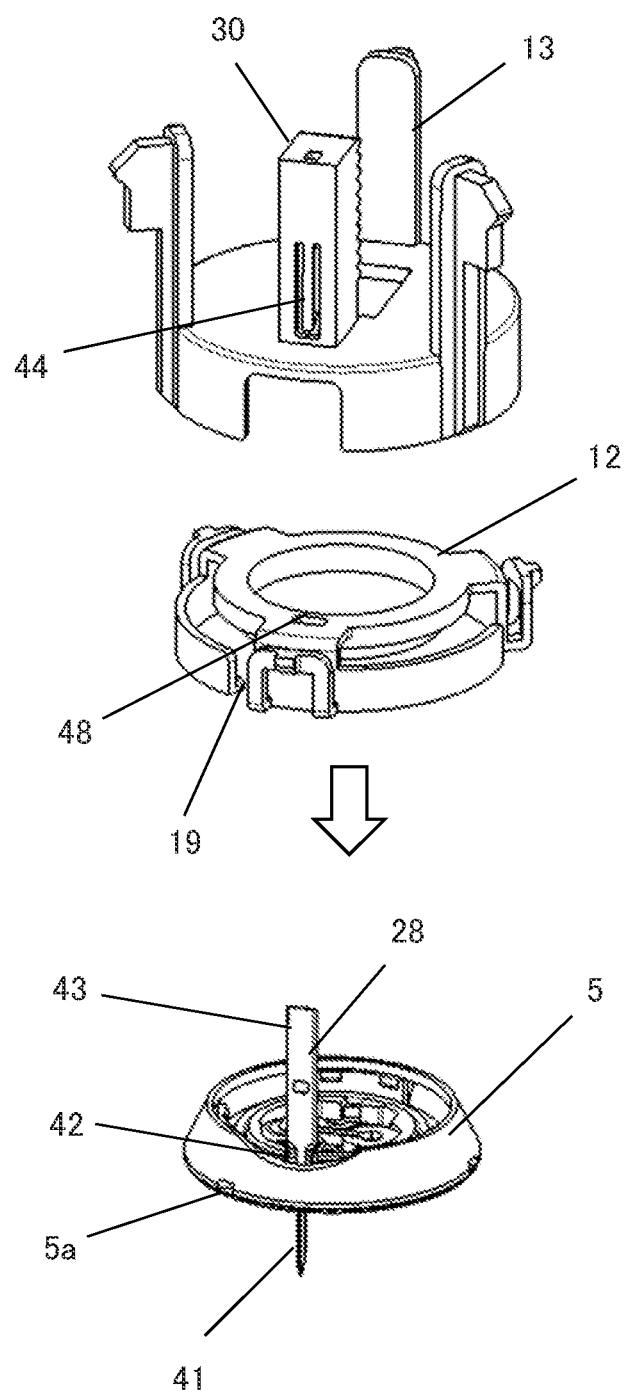
FIG. 32 is an oblique view of the procedure for mounting the guide needle of the sensor insertion device in FIG. 2.
Figure 37:
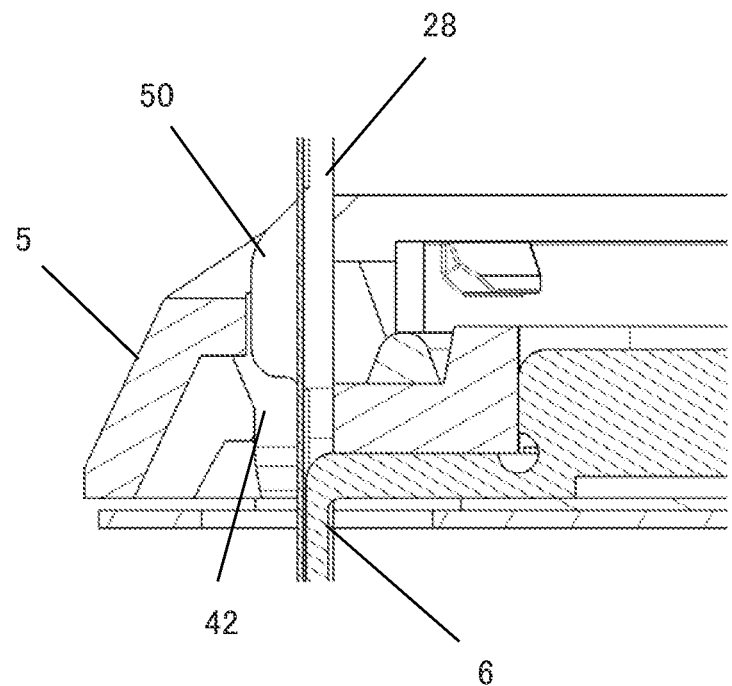
FIG. 37 is a detail cross-sectional view of the sensor base of the sensor insertion device in FIG. 2.
Figure 38:
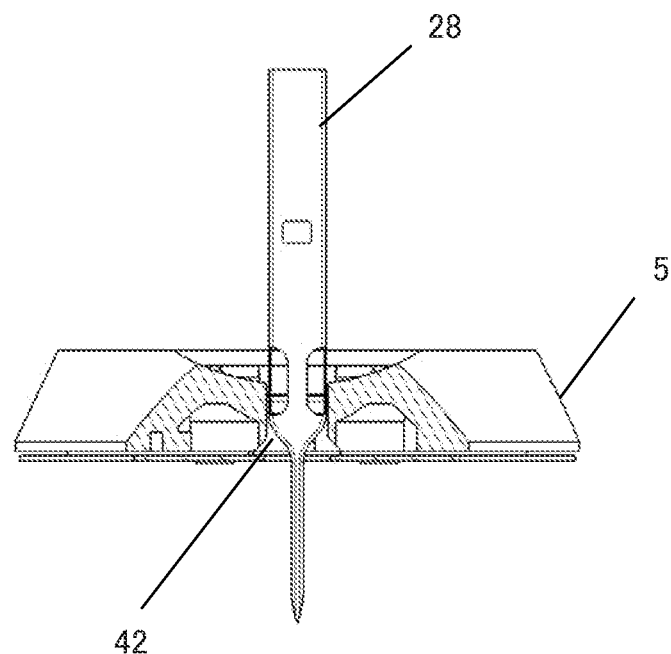
FIG. 38 is a partially cutaway side view of the sensor base of the sensor insertion device in FIG. 2.
Figure 39:
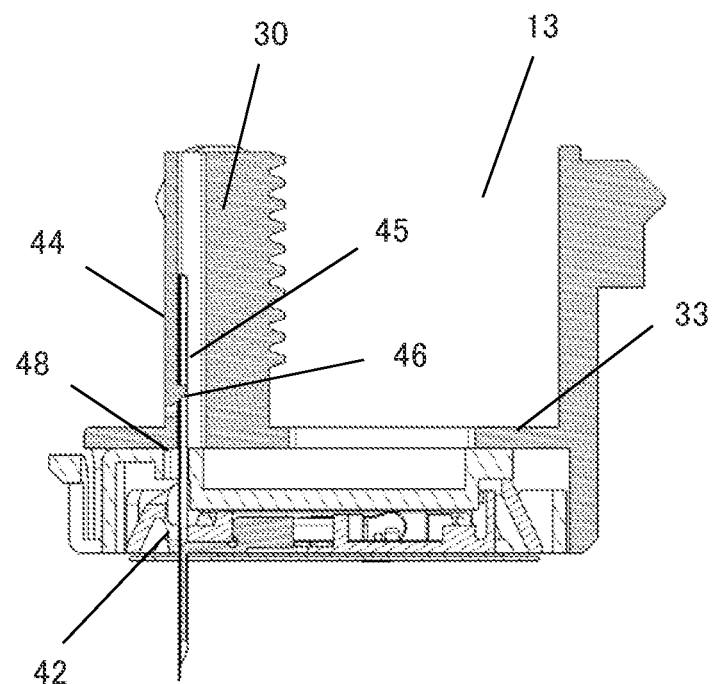
FIG. 39 is a cross-sectional view of the sensor base, the base holder, and the needle holder of the sensor insertion device in FIG. 2.
Figure 40:
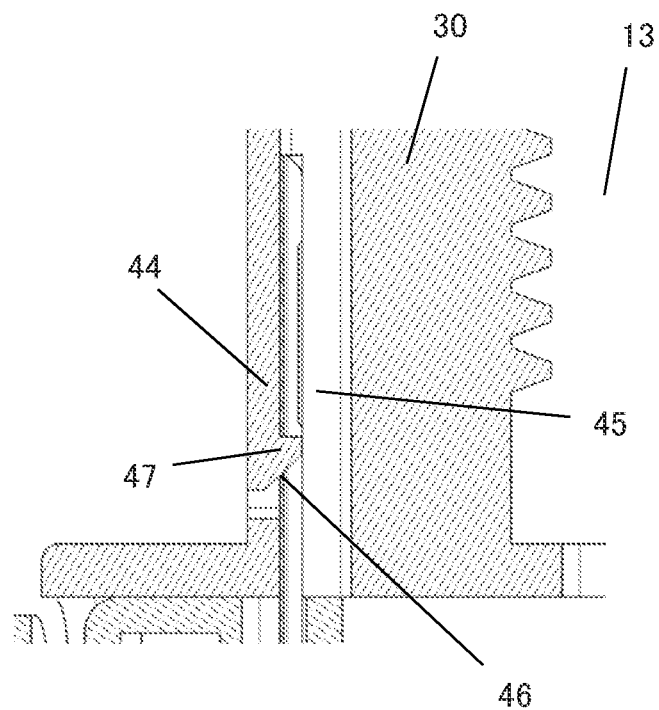
FIG. 40 is a partially enlarged cross-sectional view of the needle holder of the sensor insertion device in FIG. 2.
Figure 41:
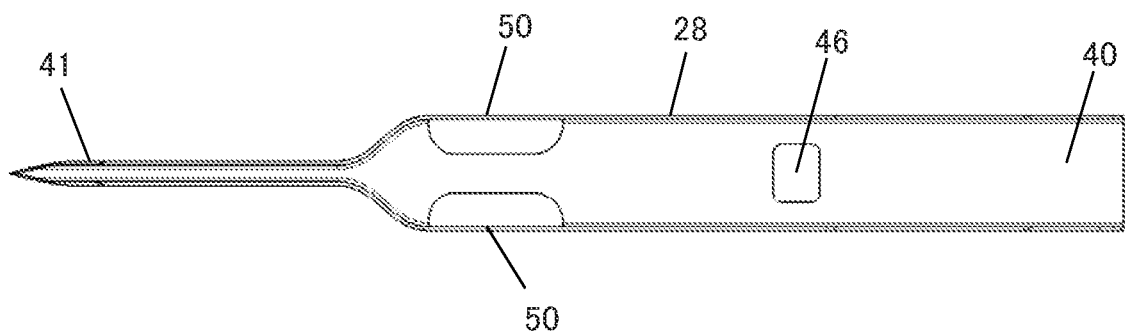
FIG. 41 is a plan view of the guide needle of the sensor insertion device in FIG. 2.

Next, the guide needle 28 is inserted into a second through-hole 48 formed in the top plate 15 of the base holder 12 (see FIGS. 32, 37, and 38). At this point, the sensor base 5 is held by the base holder 12.

The base holder 12 must be positioned in the circumferential direction with respect to the sensor base 5 so that the first through-hole 42 is aligned with the second through-hole 48 in the up and down direction. As discussed above, the protrusions 19 of the base holder 12 engage with the recesses 5a of the sensor base 5. Consequently, at the same time as the holding of the sensor base 5, the base holder 12 is positioned, the through-holes 42 and 48 are aligned with each other, and the guide needle 28 is inserted into the sensor base 5 and the base holder 12.

Figure 33:
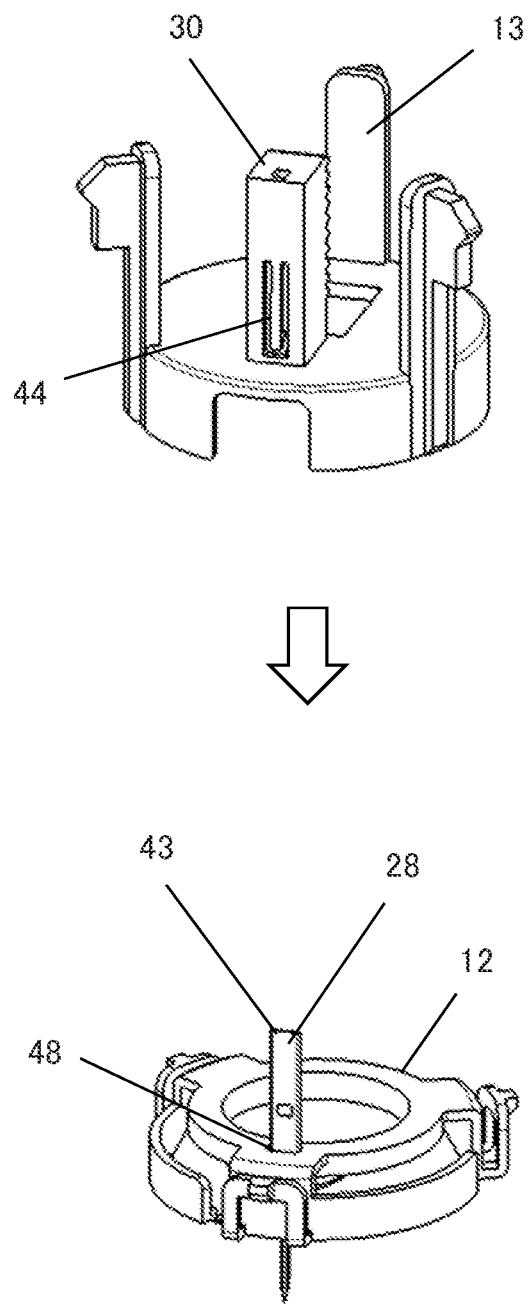
FIG. 33 is an oblique view of the procedure for mounting the guide needle of the sensor insertion device in FIG. 2.
Figure 34:
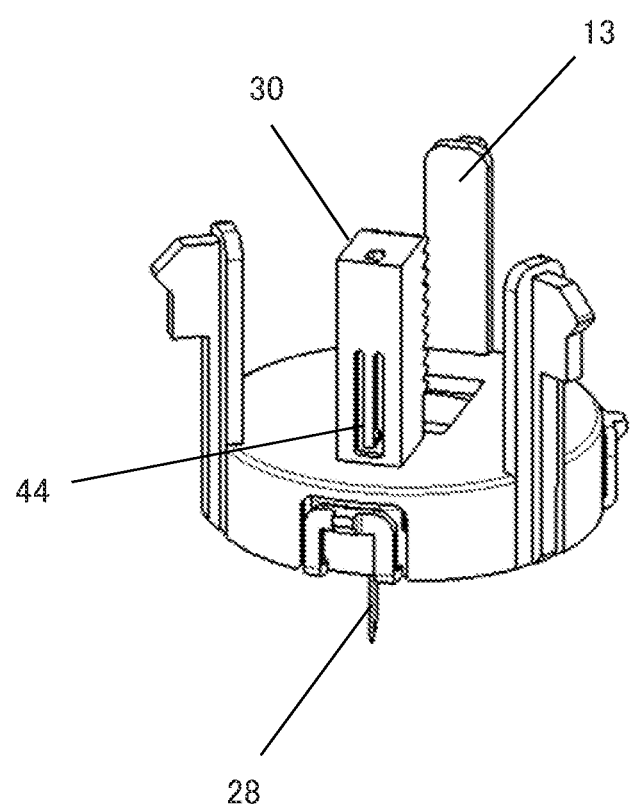
FIG. 34 is an oblique view of the procedure for mounting the guide needle of the sensor insertion device in FIG. 2.
Figure 35:
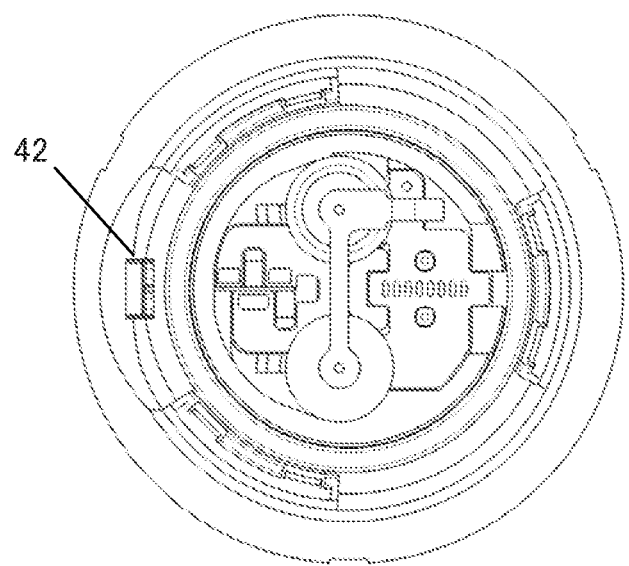
FIG. 35 is a plan view of the sensor base of the sensor insertion device in FIG. 2.

The attachment portion 40 of the guide needle 28 protrudes upward from the base holder 12 (see FIG. 33). Next, the guide needle 28 is held by the needle holder 13 (see FIGS. 34, 39, and 40). The needle holder 13 has a holding portion 44 that holds the guide needle 28. The needle holder 13 has a columnar portion that protrudes upward from the top plate 33 in order to form the teeth of the rack 30. The holding portion 44 is provided to the columnar portion by utilizing the surface of the rack 30 on the opposite side from the teeth. The holding portion 44 has a push-in hole 45 that extends in the up and down direction inside the columnar portion and opens at least downward, and a protrusion 47 that protrudes from the inner surface of the push-in hole 45. The attachment portion 40 of the needle holder 13 is pushed into the push-in hole 45 from below. This results in the engagement of the protrusion 47 with a mounting hole 46 of the needle holder 13. This completes the mounting of the guide needle 28.

Figure 36:
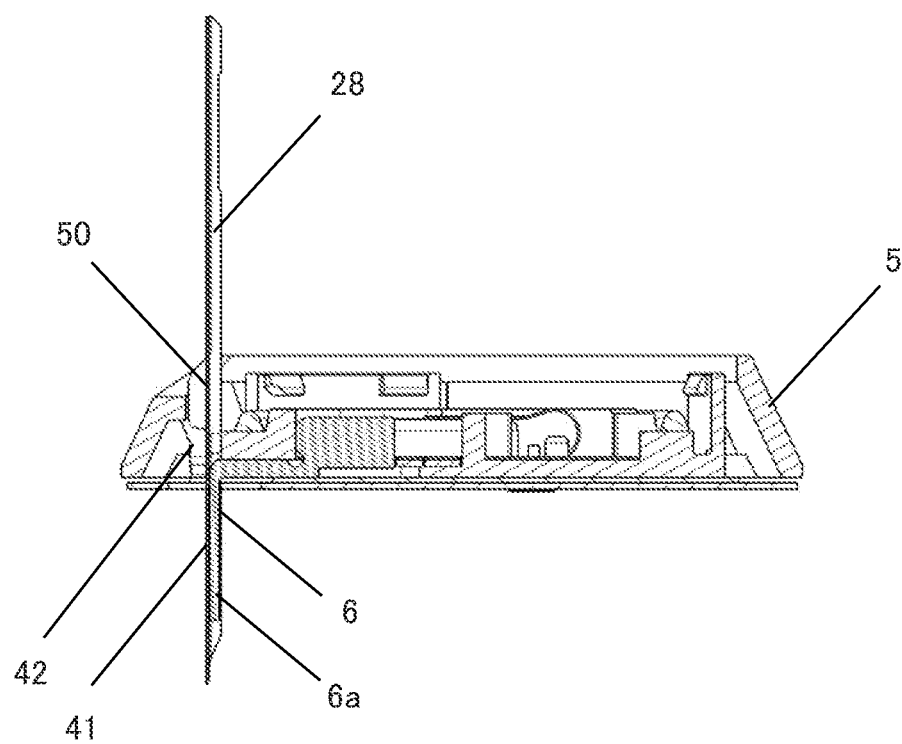
FIG. 36 is a cross-sectional view of the sensor base of the sensor insertion device in FIG. 2.

The needle holder 13 must be positioned in the circumferential direction with respect to the base holder 12 so that the second through-hole 48 is aligned with the holding portion 44 in the up and down direction. The needle holder 13 therefore has a protrusion 49 that protrudes downward from the lower surface of the top plate 23 (see FIG. 14). When the protrusion 49 is thrust into the second through-hole 48, this positions the needle holder 13 and aligns the second through-hole 48 with the holding portion 44. In order to produce this state, what is particularly important is the positional relation between the body insertion portion 41 of the guide needle 28 and the lower insertion portion 6a of the sensor unit 6 (as shown in FIG. 36, the portion that is provided on the lower end side of the sensor unit 6 and is inserted into the body 4).

In this embodiment, as shown in FIG. 30, the attachment portion 40 of the guide needle 28 is provided with a pair of engaging pieces 50 formed by cutting and lifting. The engaging pieces 50 are disposed between the mounting hole 46 and the body insertion portion 41. As shown in FIGS. 36 and 37, the engaging pieces 50 are in contact with the first through-hole 42. As shown in FIG. 38, the end face of the guide needle 28 in the width direction is also in contact with the first through-hole 42. This positions the guide needle 28 with respect to the sensor base 5. Meanwhile, the sensor unit 6 is installed in a state of being positioned on the sensor base 5. Therefore, the guide needle 28 is positioned with respect to the sensor unit 6 via the sensor base 5.

Figure 31:
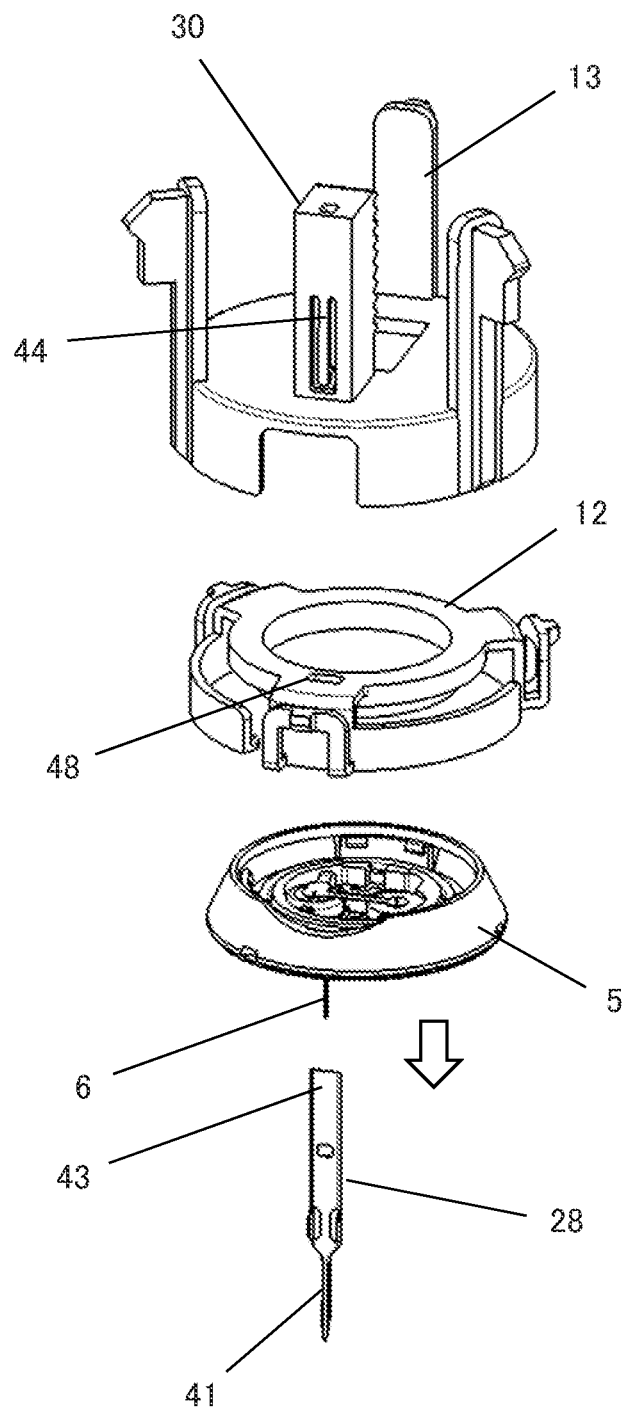
FIG. 31 is an oblique view of the procedure for mounting the guide needle of the sensor insertion device in FIG. 2.

In order to produce the state shown in FIGS. 35 to 38, the sensor base 5 is installed with respect to the guide needle 28 from above the guide needle 28, as shown in FIG. 31. At this point, the sensor unit 6 is inserted into the guide needle 28, and the state in which the sensor unit 6 is viewed from the sensor unit 6 side will be described with reference to FIGS. 47 to 49.

Figure 47:
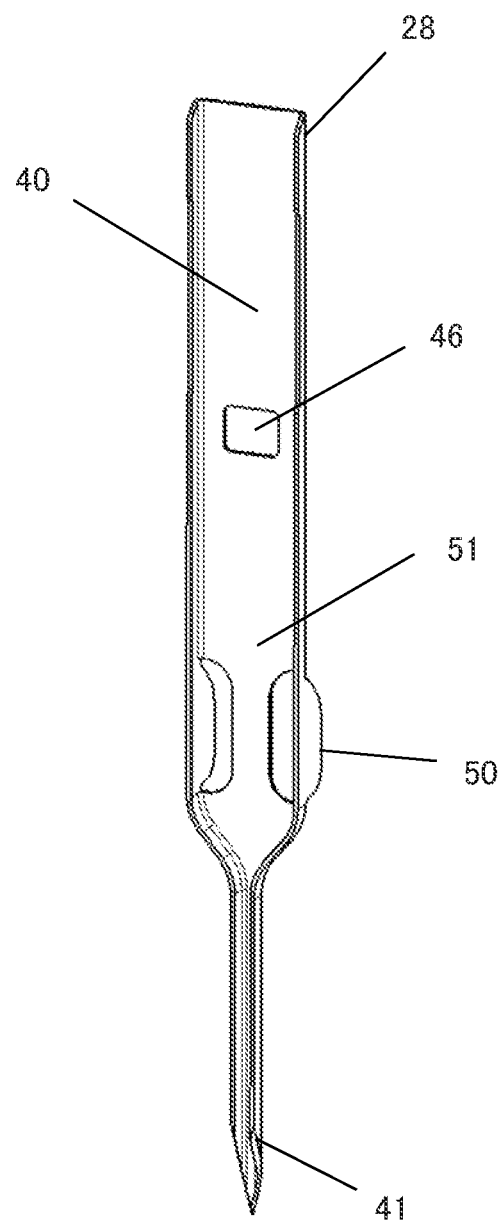
FIG. 47 is an oblique view of the guide needle of the sensor insertion device in FIG. 2.
Figure 48:
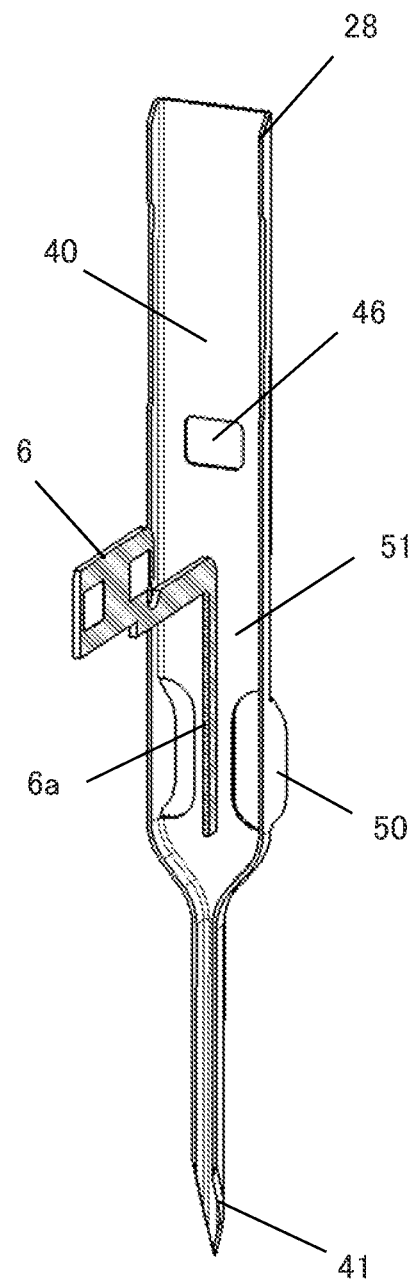
FIG. 48 is an oblique view of the guide needle of the sensor insertion device in FIG. 2.
Figure 49:
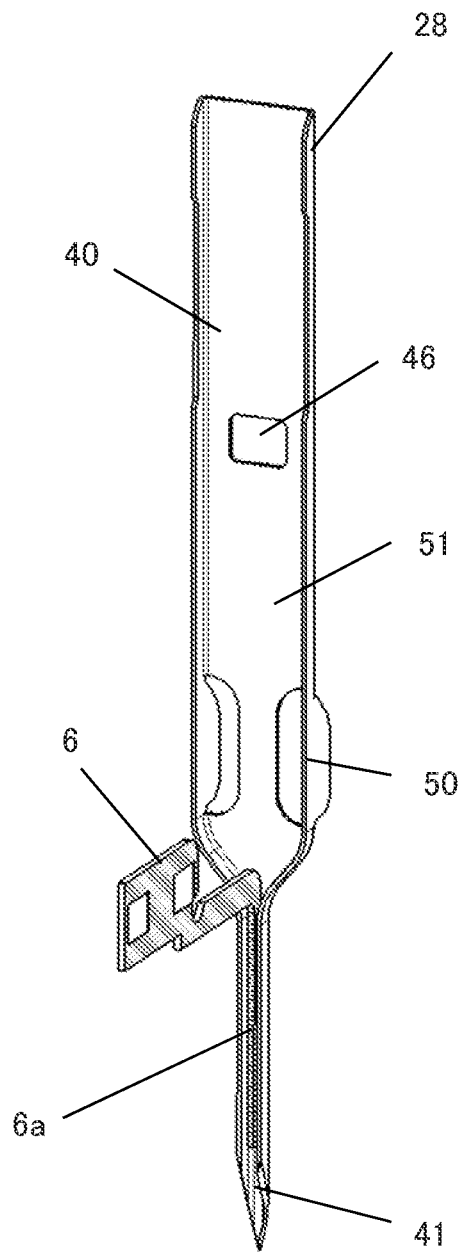
FIG. 49 is an oblique view of the guide needle of the sensor insertion device in FIG. 2.

FIG. 47 shows a state in which the guide needle 28 is held upright by a holding jig (not shown). FIG. 48 shows a state in which the sensor base 5 is installed from above the guide needle 28. FIG. 48 shows a state in which the sensor unit 6 is lowered while the lower insertion portion 6a of the sensor unit 6 is in contact with the sliding attachment portion 40 of the guide needle 28. FIG. 49 shows a state in which the installation of the sensor unit 6 is complete, that is, a state in which the sensor base 5 has been installed on the guide needle 28 as shown in FIG. 32.

What is important is that the body insertion portion 41 of the guide needle 28 does not touch the sensor unit 6, and in particular the lower insertion portion 6a, during the work of installing the guide needle 28. Since the distal end of the body insertion portion 41 of the guide needle 28 has a pointed shape, the sensor unit 6 may be damaged by just touching it slightly.

In view of this, as shown in FIGS. 47 to 49, the lower insertion portion 6a of the sensor unit 6 is installed in the body insertion portion 41 of the guide needle 28 from the sliding attachment portion 40, which is on the opposite side of the guide needle 28 from the body insertion portion 41. With this configuration, the sensor unit 6 will not be damaged by the body insertion portion 41 of the guide needle 28 during the installation work.

Also, to achieve this, the length of the guide surface 51 on the sliding attachment portion 40 of the guide needle 28 (the flat surface provided between the mounting hole 46 and the body insertion portion 41 in the sliding attachment portion 40) is greater than the length of the lower insertion portion in the sensor unit 6. As a result, the lower insertion portion of the sensor unit 6 is guided to the guide surface 51, and can be smoothly installed in the body insertion portion 41.

The body insertion portion 41 of the guide needle 28 will now be described.

As described above, the guide needle 28 has the sliding attachment portion 40 above and the body insertion portion 41 below. As shown in FIGS. 41 to 46, the body insertion portion 41 has a U-shaped cross section that is perpendicular to the lengthwise direction. Standing wall end portions 41a rise up on both sides of this U-shaped portion.

Figure 44:
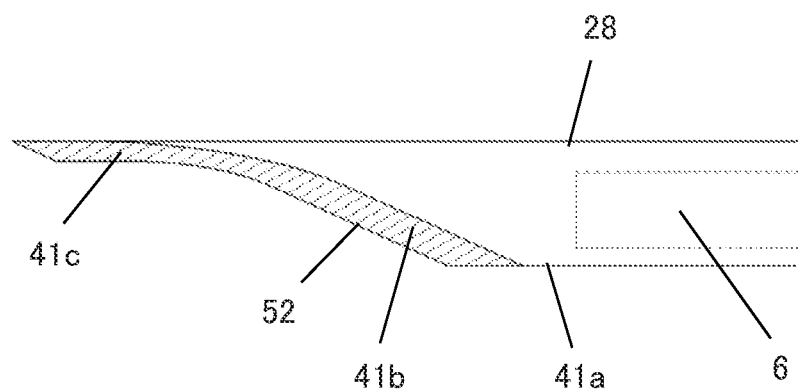
FIG. 44 is a detail front view of the lower end portion of the guide needle of the sensor insertion device in FIG. 2.
Figure 45:
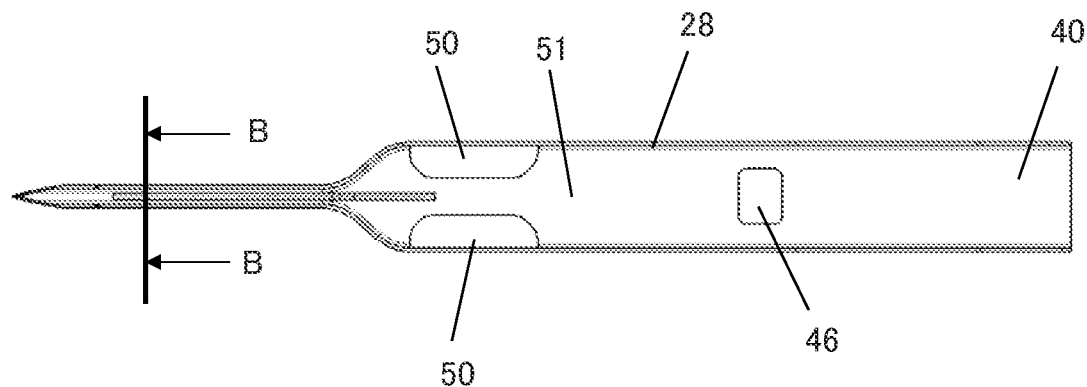
FIG. 45 is a plan view of the guide needle of the sensor insertion device in FIG. 2.
Figure 46:
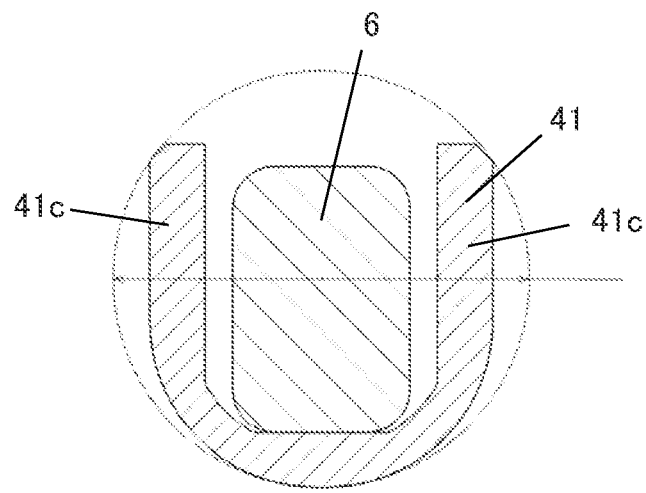
FIG. 46 is a cross-sectional view along the B-B line in FIG. 45.

As shown in FIG. 44, an end face 41b in which the height of the standing wall end portion 41a of the U-shaped portion continuously decreases toward the lower end, and a distal end portion 41c constituted by the bottom surface of the U-shaped portion are provided on the lower end side of the body insertion portion 41.

In this embodiment, the distal end portion of the body insertion portion 41 has a pointed tip shape in which the cross-sectional area continuously decreases from the U-shaped portion toward the lower end, and a continuous edged portion 52 is formed on this pointed tip portion. That is, the continuous edged portion 52 is formed from the end face 41b portion to the distal end portion 41c. As can be understood from FIG. 43, in the edged portion 52, the standing wall end portion 41a of the U-shaped portion is ground from the outside of the U-shaped portion, and edging is continuously performed to produce a sharp blade all the way to the distal end (lower end).

This is because the body insertion portion 41 of the guide needle 28 is inserted into the body 4, but if there is a step on the outer periphery of the body insertion portion 41, it will create resistance during the insertion into the body 4, and this may cause the user to feel some pain.

That is, with the guide needle of the conventional example, only the distal end portion of the lower end portion is edged, and the upper end surface portion thereof is not. Therefore, the end face 41b portion of the standing wall end portion 41a of the U-shaped portion is recognized as a step, and this tended to cause pain.

Figure 42:
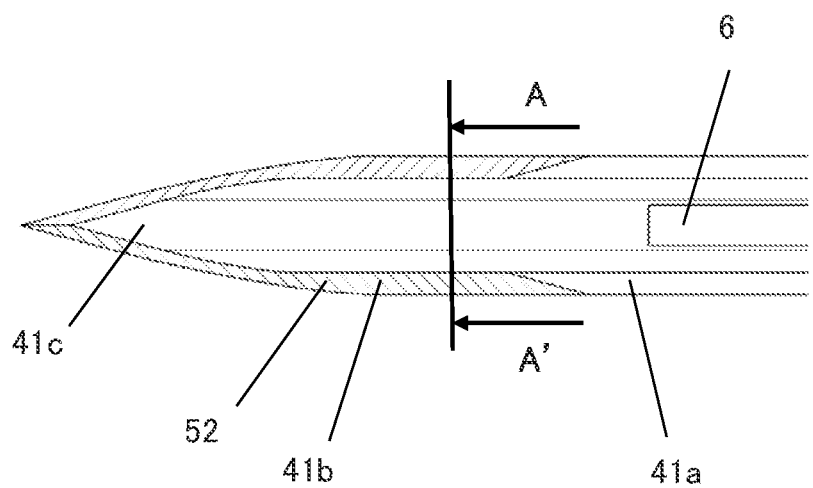
FIG. 42 is a detail plan view of the lower end portion of the guide needle of the sensor insertion device in FIG. 2.
Figure 43:
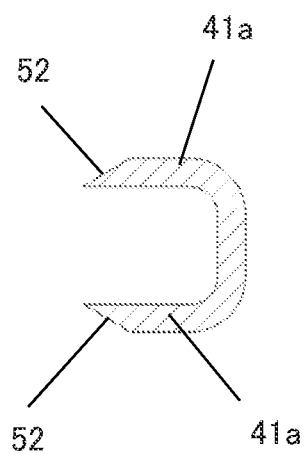
FIG. 43 is a cross-sectional view along the A-A line in FIG. 42.

In view of this, in this embodiment, the guide needle 28 is such that the continuous edged portion 52 is formed, as shown in FIGS. 42 to 44, on the portion near the lower end side of the guide needle 28, in the U-shaped portion formed for accommodating the sensor unit 6. More precisely, the continuous edged portion 52 is formed on the portion facing the skin, that is, the end face 41b portion and the distal end portion 41c, with respect to the skin of the body 4 approaching from the lower end side.

Therefore, since there is no portion (step) that is perpendicular to the skin of the body 4 approaching from the lower end side, there is less resistance during insertion into the body 4. As a result, the user experiences less pain.

The features of this embodiment will now be described.

Feature 1

The sensor insertion device 1 of this embodiment comprises the cylindrical lower case 7 and the upper case 2 that movably covers the outer periphery of the lower case 7 from above. The lower case 7 is formed in a cylindrical shape having the openings 9 and 10 on its upper and lower surfaces, respectively. The upper case 2 is formed in a cylindrical shape having the opening 11 on its lower surface and closed on its upper surface. The base holder 12 and the needle holder 13 are disposed in that order, from the bottom to the top, inside the lower case 7. The needle holder raising mechanism 14 (rack 30, pinion 32, rack 34) is disposed in the lower case 7 above the needle holder 13, and/or in the upper case 2. The base holder 12 holds the sensor base 5, which has the sensor unit 6. When the upper case 2 is pushed down, the base holder 12 and the needle holder 13 move to the lower opening 10 side on the lower surface side of the lower case 7. After this, the needle holder 13 rises, and the upper case 2 is pushed down until the opening 11 on the lower surface side thereof comes into contact with the skin of the body 4, and in this state the upper case 2 is held by the holding mechanism (the protrusions 39 and the outer peripheral wall portion below the slits 27 of the lower case 7) of the lower case 7).

As described above, in this embodiment, the base holder 12 holds the sensor base 5 having the sensor unit 6. Therefore, there is no need to attach the sensor unit 6 to the sensor base 5. Furthermore, when the upper case 2 is pushed down, the sensor base 5 is attached to the skin and the sensor unit 6 is inserted into the body 4.

Further, in a state in which the upper case 2 has been pushed down until the opening 11 on the lower surface side of the upper case 2 hits the skin of the body 4, the opening 11 on the lower surface side of the upper case 2 and the lower opening 10 on the lower surface side of the lower case 7 are in substantially the same position. Consequently, it can be determined at a glance that the device has been used. Therefore, no one will try to use the sensor insertion device 1 again, and the work is much more efficient.

In this embodiment, the protrusions 39 are formed on the lower inner peripheral surface of the upper case 2, and the outer peripheral wall portion below the slits 27 of the lower case 7 is set as a portion facing the protrusions 39. The holding mechanism may be configured such that, for example, the protrusions 39 are provided on the lower outer peripheral surface of the lower case 7 and are brought into contact with the lower inner peripheral surface of the upper case 2.

Feature 2

In the conventional example, a mechanism for guiding the downward movement of the sensor base is provided to the lower case, and a mechanism for guiding the downward movement of the needle holder is provided to the upper case. When the upper case is pushed down, the sensor base and the needle holder are guided by the corresponding guide mechanism as they move downward. However, in order to allow the upper case to move downward with respect to the lower case, an appropriate clearance is required between the upper and lower cases. Because of this clearance, there may be some looseness between the upper case may and the lower case. If the two guide mechanisms are divided into upper and lower cases as in the conventional example, the looseness may cause misalignment between the guide direction of the needle holder and the guide direction of the sensor base, and the needle holder and/or the sensor base may not move down properly. In this happens, the sensor base may not be properly attached to the skin, or the sensor unit may not be properly inserted into the body.

Therefore, the sensor insertion device 1 in this embodiment comprises the cylindrical lower case 7 and the upper case 2 movably covers the outer periphery of the lower case 7 from above. The lower case 7 has a cylindrical shape with the openings 9 and 10 on its upper and lower surfaces. The upper case 2 has a cylindrical shape with an opening 11 in the lower surface and a closed upper surface. In the lower case 7, the base holder 12 and the needle holder 13 are disposed in that order, from the bottom to the top. The needle holder raising mechanism 14 is disposed in the upper case 2 and/or the lower case 7 above the needle holder 13. The base holder 12 holds the sensor base 5 having the sensor unit 6. The lower case 7 is provided with the grooves 20 and the slits 27 as guiding means for guiding the downward motion of the base holder 12 and the needle holder 13.

That is, the base holder 12 can be guided by the grooves 20 while moving downward, and the needle holder 13 can be guided by the slits 27 while moving up and down.

Therefore, in this embodiment, the sensor base 5 is properly attached to the body 4 and the sensor unit 6 is properly inserted into the body 4. That is, the needle holder 13 and the sensor base 5 having the sensor unit 6 are both moved downward by the guiding means provided to the lower case 7. Therefore, the positional relation between the sensor base 5 and the needle holder 13 during downward movement is stable. As a result, the sensor base 5 is properly attached to the body 4 and the sensor unit 6 is properly inserted into the body 4.

Feature 3

In the conventional example, protrusions for holding the sensor base are provided to the lower case. The holding by these protrusions is released immediately after the upper case begins to move downward. Therefore, the sensor base may fall off of the sensor insertion device before the sensor base is attached to the body.

In view of this, the sensor insertion device 1 in this embodiment comprises the cylindrical lower case 7 and the upper case 2 that movably covers the outer circumference of the lower case 7 from above. The lower case 7 has a cylindrical shape with the openings 9 and 10 on its upper and lower surfaces. The upper case 2 has a cylindrical shape with an opening 11 in the lower surface and a closed upper surface. In the lower case 7, the base holder 12 and the needle holder 13 are disposed in that order, from the bottom to the top. The needle holder raising mechanism 14 (rack 30, pinion 32, rack 34) is disposed in the upper case 2 and/or the lower case 7 above the needle holder 13.

The base holder 12 has the holding levers 18 that are fixed at one end to the base holder 12 and are freely displaceable in the inward and outward directions at the other end, on the outer circumference of the sensor base 5. On the other end side of the holding levers 18, the protrusions 19 are formed that engage with the recesses 5a on the outer periphery of the sensor base 5. The needle holder 13 is provided with the restraining walls 26 that prevent the protrusions 19 of the holding levers 18 from moving outward on the outer peripheral portion of the base holder 12.

That is, in this embodiment, the sensor base 5 is in a state of being held by the holding levers 18 of the base holder 12. The protrusions 19 of the holding levers 18 are prevented from moving outward by the restraining walls 26 provided to the needle holder 13.

Therefore, the sensor base 5 remains properly held by the base holder 12 until the sensor base 5 held by the base holder 12 is attached to the body 4, and the sensor unit 6 is inserted into the body 4 by the guide needle 28 of the needle holder 13. As a result, the sensor base 5 is prevented from being accidentally dropped before being attached to the body 4.

Feature 4

In the conventional example, the sensor unit is inserted into the body along with the guide needle. The tip of the guide needle is therefore extremely sharp. In placing the sensor unit on the guide needle, if the tip of the guide needle should touch the insertion part of the sensor unit even slightly when the guide needle is moved relative to the sensor unit in the up and down direction, the sensor unit may be damaged. If this happens, the required measurement cannot be performed properly.

The sensor insertion device 1 of this embodiment therefore comprises the cylindrical lower case 7 and the upper case 2 that movably covers the outer circumference of the lower case 7 from above. The lower case 7 has a cylindrical shape having openings 9 and 10 on its upper and lower surfaces. The upper case 2 has a cylindrical shape with the opening 11 on its lower surface and a closed upper surface. In the lower case 7, the base holder 12 and the needle holder 13 are disposed in that order, from the bottom to the top. The needle holder raising mechanism 14 (rack 30, pinion 32, rack 34) is disposed in the upper case 2 and/or the lower case 7 above the needle holder 13.

Through-holes 42 and 48 through which the guide needle 28 passes are formed in the sensor base 5 and the base holder 12. The holding portion 44 that holds the upper portion of the guide needle 28 is formed on the needle holder 13.

The sensor base 5 and the base holder 12 are provided with a first positioning portion for aligning the through-holes 42 and 48 through which the guide needle 28 passes in the sensor base 5 and the base holder 12. In this embodiment, the first positioning portion is configured such that the protrusions 19 of the base holder 12 engage with the recesses 5a on the outer periphery of the sensor base 5, and this is what aligns the through-hole 42 of the sensor base 5 with the through-hole 48 of the base holder 12.

Also, the base holder 12 and the needle holder 13 are provided with a second positioning portion for aligning the through-hole 48 of the base holder 12 with the holding portion 44 of the needle holder 13. In this embodiment, as shown in FIG. 14, the second positioning portion is configured to protrude downward toward the lower surface side of the top plate 23 of the needle holder 13, and to force the protrusion 49 into the through-hole 48 of the base holder 12 (see FIG. 30). That is, when the protrusion 49 of the needle holder 13 is forced into the through-hole 48 of the base holder 12, the through-hole 48 of the base holder 12 lines up with the holding portion 44 of the needle holder 13.

As described above, in this embodiment, when the sensor base 5, the base holder 12, and the needle holder 13 are attached to the guide needle 28 from the upper part of the guide needle 28, they are held in the holding portion 44 of the needle holder 13.

Since the guide needle 28 is longer than the insertion portion of the sensor unit 6, when the sensor base 5, the base holder 12, and the needle holder 13 are attached from above the guide needle 28 as described above, the sharp body insertion portion 41 will not damage the insertion portion of the sensor unit 6 at the lower part of the guide needle 28. As a result, an appropriate measurement can be made using the sensor unit 6.

Feature 5

In the conventional example, the sensor unit is included in the guide needle and is inserted into the body together with the guide needle. The tip of the guide needle is formed sharply so that it will be smoothly inserted into the body upon first touching the body, while the upper portion of the guide needle has a U-shaped cross section to include the guide needle. The U-shaped portion is also inserted into the body, but the end face of the plate forming the U-shaped portion creates a strong resistance to insertion, and this may cause the user to feel some pain.

In view of this, the sensor insertion device 1 of this embodiment comprises the cylindrical lower case 7 and the upper case 2 that movably covers the outer circumference of the lower case 7 from above. The lower case 7 has a cylindrical shape having openings 9 and 10 on its upper and lower surfaces. The upper case 2 has a cylindrical shape with the opening 11 on its lower surface and a closed upper surface. In the lower case 7, the base holder 12 and the needle holder 13 are disposed in that order, from the bottom to the top. The needle holder raising mechanism 14 (rack 30, pinion 32, rack 34) is disposed in the upper case 2 and/or the lower case 7 above the needle holder 13.

Through-holes 42 and 48 through which the guide needle 28 passes are formed in the sensor base 5 and the base holder 12. The needle holder 13 is formed with a holding portion 44 that holds the upper portion of the guide needle 28. The guide needle 28 has an upper sliding attachment portion 40 provided as an upward attachment portion, and a lower body insertion portion 41. The body insertion portion 41 has a U-shaped cross section that is perpendicular to the lengthwise direction. The distal end portion has a sharp tip shape in which the cross-sectional area decreases continuously from the U-shaped portion toward the lower end, and a continuous edged portion 52 is formed in the sharp tip portion.

The guide needle 28 in this embodiment also has a U-shaped cross section that is perpendicular to the lengthwise direction in order to include the insertion portion of the sensor unit 6. The distal end portion has a sharp tip shape in which the cross-sectional area continuously decreases from the U-shaped portion toward the lower end, and the continuous edged portion 52 is formed in the sharp tip portion. Therefore, no strong resistance is produced when the body insertion portion 41 of the guide needle 28 is inserted into the body 4. As a result, the pain experienced by the user when the guide needle 28 is inserted can be reduced.

Addenda

The present invention can also be expressed as follows.

Addendum A1

A sensor insertion device, comprising:
- a lower case formed in a cylindrical shape that has an upper opening at the upper end and a lower opening at the lower end;
- an upper case formed in a cylindrical shape that has an opening at the lower end and is closed on the upper surface, which covers the outer periphery of the lower case from above so as to be movable downward;
- a base holder that is disposed inside the lower case;
- a sensor base that has a sensor unit and is held in the base holder;
- a needle holder that is disposed above the base holder inside the lower case;
- a needle holder raising mechanism that is disposed above the needle holder inside the lower case and/or the upper case; and a guide mechanism that is provided to the lower case to guide the downward movement of a downward moving body, including the base holder and the needle holder.

Addendum A2

The sensor insertion device according to addendum A1, wherein the guide mechanism has a groove (20) that extends in the up and down direction on the inner peripheral surface of the lower case, and an engaging piece (17) that slides in the groove 20 and is provided to the outer peripheral portion of the downward moving body.

Addendum A3

The sensor insertion device according to addendum A1, wherein the guide mechanism has a slit (27) that extends downward from the upper opening of the lower case, and a first protrusion (25) that slides in this slit and is provided to the outer peripheral portion of the downward moving body.

Addendum A4

The sensor insertion device according to addendum A1, wherein the guide mechanism has a plurality of slits (27) that extend downward from the upper opening of the lower case, and a groove (20) that extends in the up and down direction in the portion of the inner peripheral surface of the lower case that is between the slits in the circumferential direction.

Addendum A5

The sensor insertion device according to addendum A4, wherein the guide mechanism includes an engaging piece (17) that is provided on the outer peripheral portion of the base holder and engages with the groove, and a plurality of first protrusions (25) that are provided on the outer peripheral portion of the needle holder and engage with the plurality of slits.

Addendum A6

The sensor insertion device according to addendum 5, wherein the groove extends below the lower case with respect to the slit.

Addendum A7

The sensor insertion device according to addendum A5 or A6, wherein the groove is provided with a standby position setting unit that holds the base holder in a standby position, and the outer peripheral surface of the lower case is provided with an upper position setting unit that holds the upper case in an upper position above the standby position setting unit.

Addendum A8

The sensor insertion device according to addendum A7, wherein the upper position setting unit is formed by a second protrusion (38) that protrudes in the outer peripheral direction, and in the upper case, a third protrusion (39) is formed which protrudes in the inner peripheral direction from the upper and lower parts with respect to the second protrusion, in a state of being held in the upper position by the second protrusion.

Addendum B1

A sensor insertion device, comprising:
a lower case formed in a cylindrical shape that has an upper opening at the upper end and a lower opening at the lower end;
an upper case formed in a cylindrical shape that has an opening at the lower end and is closed on the upper surface, which covers the outer periphery of the lower case from above so as to be movable downward;
a base holder that is disposed inside the lower case;
a sensor base that is held in the base holder;
a needle holder that is disposed above the base holder inside the lower case, and to which a guide needle is attached; and
a needle holder raising mechanism that is disposed above the needle holder inside the lower case and/or the upper case,
wherein the base holder has a holding lever that is disposed more toward the outer periphery than the sensor base, is fixed at one end to the base holder, and is freely displaceable in the inward and outward directions on the other end side, and a protrusion that engages with the outer peripheral portion of the sensor base is formed on the other end side of the holding lever, and
the needle holder has a restraining wall that is disposed more toward the outer periphery than the base holder, and that suppresses the outward movement of the protrusion of the holding lever.

Addendum B2

The sensor insertion device according to addendum B1, wherein the base holder has a plurality of the holding levers.

Addendum C1

A sensor insertion device, comprising:
a lower case formed in a cylindrical shape that has an upper opening at the upper end and a lower opening at the lower end;
an upper case formed in a cylindrical shape that has an opening at the lower end and is closed on the upper surface, which covers the outer periphery of the lower case from above so as to be movable downward;
a base holder that is disposed inside the lower case;
a sensor base that has a sensor unit and is held in the base holder;
a needle holder that is disposed above the base holder inside the lower case, and to which a guide needle is attached; and
a needle holder raising mechanism that is disposed above the needle holder inside the lower case and/or the upper case,
wherein the sensor base has a first through-hole (42) through which the guide needle passes, the base holder has a second through-hole (48) through which the guide needle passes, and the needle holder has a holding portion that holds the upper part of the guide needle,
the sensor base and the base holder are provided with a first positioning portion for aligning the first through-hole and the second through-hole, and
the base holder and the needle holder are provided with a second positioning portion for aligning the second through-hole (48) and the holding portion.

Addendum C2

The sensor insertion device according to addendum C1, wherein the guide needle has an upper attachment portion and a lower body insertion portion, and
the attachment portion is provided with a cut-and-lift piece that abuts the opening edge of the first through-hole (42).

Addendum C3

The sensor insertion device according to addendum C2, wherein the attachment portion is provided with a guide surface for the sensor unit.

Addendum C4

The sensor insertion device according to addendum C3, wherein the sensor unit has an insertion portion (6*a*) for insertion into the body, and the length of the guide surface is greater than the length of the insertion portion.

Addendum D1

A sensor insertion device, comprising:
a lower case formed in a cylindrical shape having an upper opening at the upper end and a lower opening at the lower end;
an upper case formed in a cylindrical shape that has an opening at the lower end and is closed on the upper surface, which covers the outer periphery of the lower case from above so as to be movable downward;
a base holder that is disposed in the lower case;
a sensor base that is held in the base holder;
a needle holder disposed in the lower case and to which a guide needle is attached; and
a needle holder raising mechanism that is disposed inside the lower case and/or the upper case,
wherein the guide needle has an upper attachment portion and a lower body insertion portion, and
the body insertion portion includes a U-shaped portion having a U-shaped cross section perpendicular to the lengthwise direction, and a sharp tip portion that is formed at the distal end portion of the U-shaped portion and in which the cross-sectional area continuously decreases from the U-shaped portion toward the lower end, and a continuous edged portion is formed in the sharp tip portion.

Addendum D2

The sensor insertion device according to addendum D1, wherein the sharp tip portion is formed by polishing the pair of standing wall end portions constituting the U-shaped portion from the outside.

INDUSTRIAL APPLICABILITY

The present invention is expected to find widespread use as, for example, a sensor insertion device for inserting a sensor unit for performing continuous blood glucose measurement into a user's body.

REFERENCE SIGNS LIST 1 sensor insertion device
2 upper case
2a skin contact portion
3 cap
4 body
5 sensor base
5a recess
6 sensor unit
6a insertion portion
7 lower case
8 transmitter
9 upper opening
10 lower opening
11 opening
12 base holder
13 needle holder
14 needle holder raising mechanism
15 top plate
16 hanging piece
17 engaging piece
18 holding lever
19 protrusion
20 groove
21 protrusion
22 groove
23 top plate
24 riser
25 protrusion
26 restraining wall
27 slit
28 guide needle
29 opening
30 rack
31 rotating shaft
32 pinion
33 top plate
34 rack
35 engaging portion
36 skin tape
37 engaging portion
38 protrusion
39 protrusion
40 attachment portion
41 body insertion portion
41a standing wall edge portion
41b end face
41c distal end portion
42 first through-hole
43 upper portion
44 holding portion
45 push-in hole
46 mounting hole
47 protrusion
48 second through-hole
49 protrusion
50 engaging portion
51 guide surface
52 edged portion

The invention claimed is:

1. A sensor insertion device, comprising:
a lower case formed in a cylindrical shape having an upper opening at an upper end and a lower opening at a lower end;
an upper case formed in a cylindrical shape that has an opening at a lower end and is closed on an upper surface, which covers an outer periphery of the lower case from above so as to be movable downward;
a base holder that is disposed inside the lower case and holds a sensor base having a sensor unit;
a needle holder that is disposed above the base holder inside the lower case; and
a needle holder raising mechanism that is disposed above the needle holder, the needle holder raising mechanism being disposed inside the lower case or the upper case,
wherein the upper case, the base holder, the needle holder and the needle holder raising mechanism are configured such that when the upper case is pushed down, the base holder and the needle holder move toward the lower opening of the lower case, and then the needle holder is raised by the needle holder raising mechanism,
wherein a holding mechanism is provided to an inner peripheral surface of the upper case or an outer peripheral surface of the lower case, and
wherein the holding mechanism is configured to hold the upper case on the lower case in a state in which the upper case has been pushed down until an axial end surface of the upper case formed at an edge of the opening of the upper case is at a same axial position as an axial end surface of the lower case formed at an edge of the lower opening of the lower case, and thereby in a state in which the lower case is completely housed in the upper case, and wherein the needle holder raising mechanism comprises
   a pinion arranged on a rotating shaft which is rotatably supported by the lower case,
   a first rack extending upward from a top plate of the needle holder and that engages with the pinion, and
   a second rack extending downward from the lower surface of the upper case such that the first rack and the second rack face each other via the pinion in a radial direction of the rotating shaft in a state in which the second rack is engaged with the pinion,
wherein the needle holder raising mechanism is configured to begin raising the needle holder when the upper case is pushed down to a point at which a lower end portion of the second rack engages with the pinion, and to raise the needle holder by raising the first rack engaged with the pinion when the second rack is pushed down with respect to the pinion in the state in which the second rack is engaged with the pinion.

2. The sensor insertion device according to claim 1, wherein the holding mechanism has a first protrusion that is provided to either the inner peripheral surface of the upper case or the outer peripheral surface of the lower case, and an engaging portion that is provided to the lower case or the upper case and is engaged with the first protrusion.

3. The sensor insertion device according to claim 2, wherein the first protrusion is provided to a lower portion of either the inner peripheral surface of the upper case or the outer peripheral surface of the lower case, and the engaging portion is provided to a lower portion of the lower case or the upper case.

4. The sensor insertion device according to claim 2, wherein the lower case has a slit extending downward from the upper opening, and
the first protrusion is provided to the upper case, and the engaging portion is provided at a part of the outer peripheral surface of the lower case that is below a lower end of the slit.

5. The sensor insertion device according to claim 1, wherein the axial end surface of the upper case is formed as a skin contact portion.

6. The sensor insertion device according to claim 1, wherein the lower case has a slit extending downward from the upper opening,
the needle holder has a protrusion that goes through the slit and protrudes outward from the outer peripheral surface of the lower case, and
the holding mechanism includes the protrusion of the needle holder and a portion of the inner peripheral surface of the upper case that comes into contact with the protrusion of the needle holder.

7. The sensor insertion device according to claim 6, wherein the protrusion of the needle holder is provided so as to be able to move up and down in the slit.

8. The sensor insertion device according to claim 6, wherein the needle holder has a top plate and a riser extending upward from the top plate, and
the protrusion of the needle holder is provided to an upper end portion of the riser, and is engaged with the inner peripheral surface of the upper case by an elastic force of the riser.

* * * * *